United States Patent
Mohan

(10) Patent No.: US 10,073,099 B2
(45) Date of Patent: Sep. 11, 2018

(54) METHODS AND DIAGNOSTICS FOR CANCER DETECTION AND TREATMENT MONITORING

(71) Applicant: University of New England, Biddeford, ME (US)

(72) Inventor: Srinidi Mohan, Biddeford, ME (US)

(73) Assignee: University of New England, Biddeford, ME (US)

( * ) Notice: Subject to any disclaimer, the term of this patent is extended or adjusted under 35 U.S.C. 154(b) by 0 days.

(21) Appl. No.: 15/272,841

(22) Filed: Sep. 22, 2016

(65) Prior Publication Data

US 2017/0089902 A1 Mar. 30, 2017

Related U.S. Application Data

(60) Provisional application No. 62/232,816, filed on Sep. 25, 2015, provisional application No. 62/295,694, filed on Feb. 16, 2016, provisional application No. 62/364,539, filed on Jul. 20, 2016.

(51) Int. Cl.
    *G01N 33/53* (2006.01)
    *G01N 33/574* (2006.01)
    *C07K 16/44* (2006.01)
    *G01N 33/68* (2006.01)

(52) U.S. Cl.
    CPC ....... *G01N 33/57415* (2013.01); *C07K 16/44* (2013.01); *G01N 33/57484* (2013.01); *G01N 33/6812* (2013.01); *C07K 2317/20* (2013.01)

(58) Field of Classification Search
    None
    See application file for complete search history.

(56) References Cited

U.S. PATENT DOCUMENTS

| 2008/0052007 A1 | 2/2008 | Yu et al. |
| 2011/0039788 A1 | 2/2011 | Briegel |
| 2012/0046199 A1 | 2/2012 | Ruijtenbeek et al. |

OTHER PUBLICATIONS

Pervin et al (Nitric Oxide, 2008, 19:103-106, IDS).*
Pow et al (Cell Tissue Research, 1997, 290:501-514).*
Mohan et al. "N w-hydroxy-L-arginine as a novel ethnic specific indicator of estrogen-negative breast cancer", Amino Acids, Aug. 9, 2016, vol. 48, pp. 2693-2698. Entire Document.
Pervin et al. "Nitric oxide, N omega-hydroxy-L-arginine and breast cancer", Nitric Oxide, Apr. 24, 2008, vol. 19, pp. 103-106. Entire Document.
Singh et al. "Proteomic identification of mitochondrial targets of arginase in human breast cancer", PLoS One, Nov. 5, 2012, vol. 8, e79242, pp. 1-15. Entire Document.
International Search Report for International Application No. PCT/US2016/053055 dated Dec. 20, 2016.

* cited by examiner

*Primary Examiner* — Laura B Goddard
(74) *Attorney, Agent, or Firm* — Greenberg Traurig, LLP; Roman Fayerberg

(57) ABSTRACT

Methods and diagnostic compositions for monitoring ER− breast cancer are disclosed. In some aspects, a method for detecting ER− breast cancer in a subject comprises obtaining a subject sample from a subject suffering from breast cancer; determining a level of NOHA in the subject sample; and comparing the level of NOHA obtained from the subject sample to the level of NOHA in a control sample, wherein a lower level of NOHA in the subject sample indicates presence of ER− breast cancer in the subject.

12 Claims, 17 Drawing Sheets

Specification includes a Sequence Listing.

FIG. 4

Alignments

```
                                              <----FR2-IMGT---->
                                              K  P  A  P  A
Query_1       271  AAAACCAGCACCAGCCC  287
IGKV1D-43*01  114  ....AA.K.A         130
                   K  P  A  K  A
```

V  88.2% (15/17)

Lambda        K      H
  1.10        0.333  0.549

Gapped
Lambda        K      H
  1.08        0.280  0.540

Effective search space used: 3822646

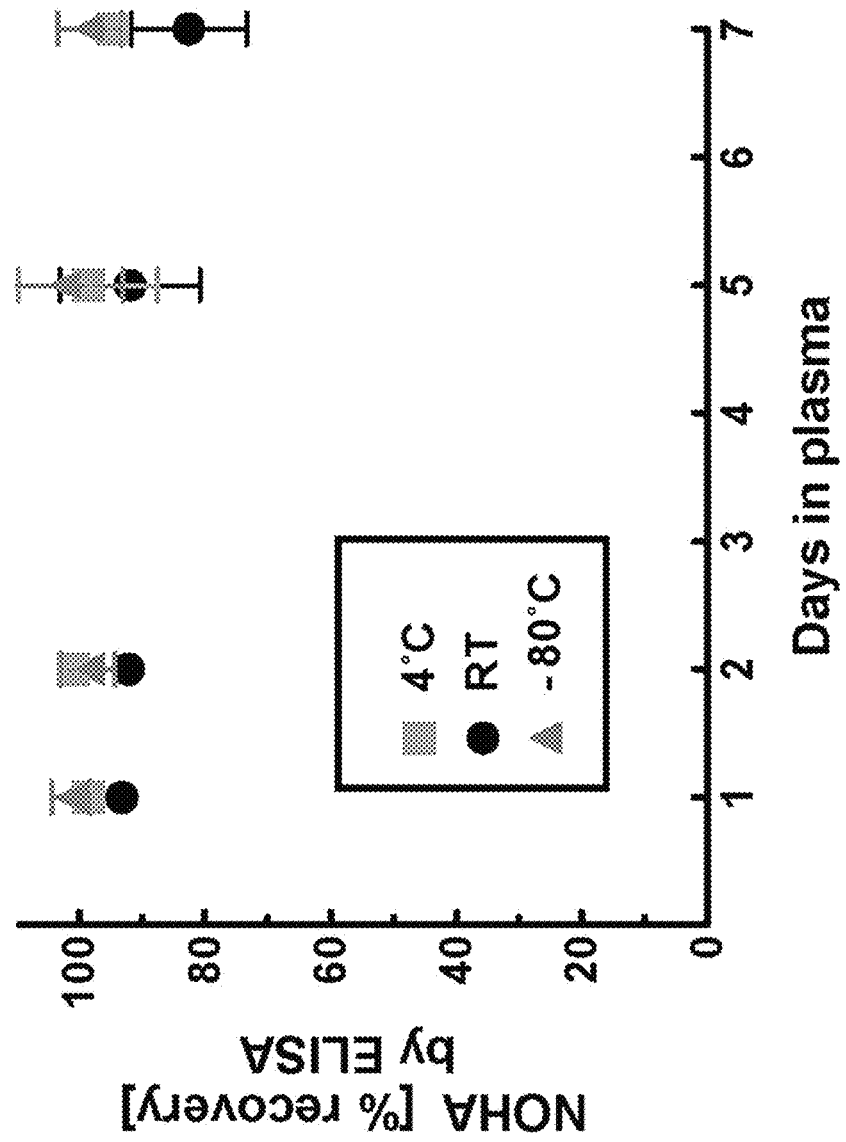

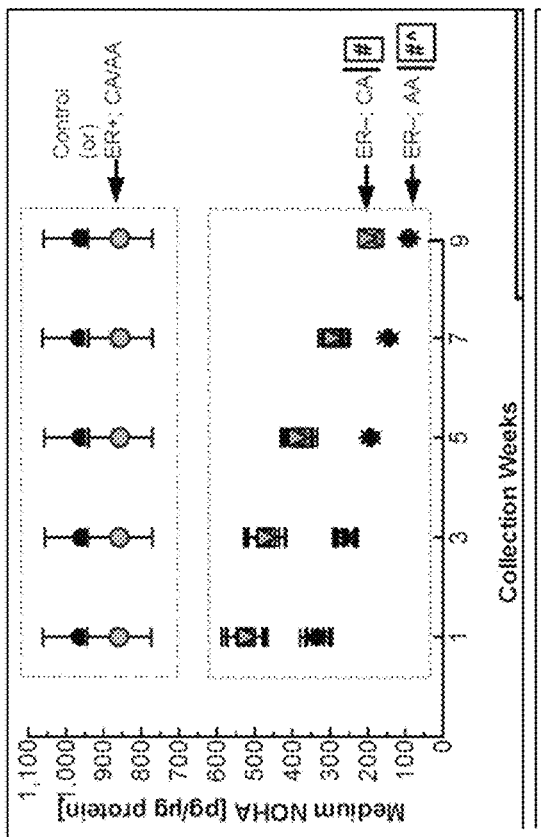
FIG. 8A
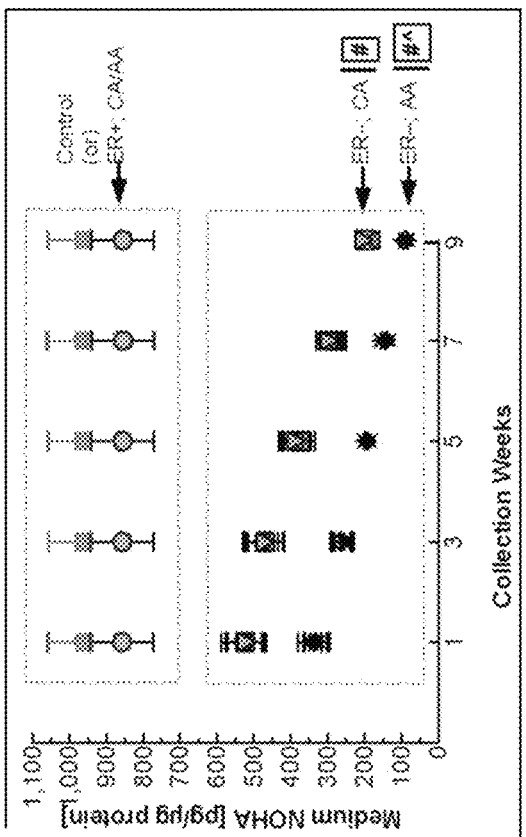
FIG. 8B
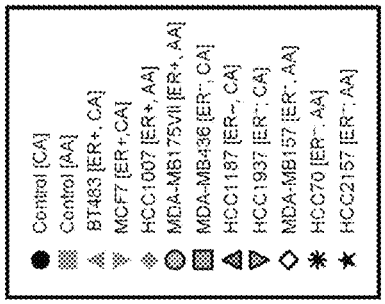

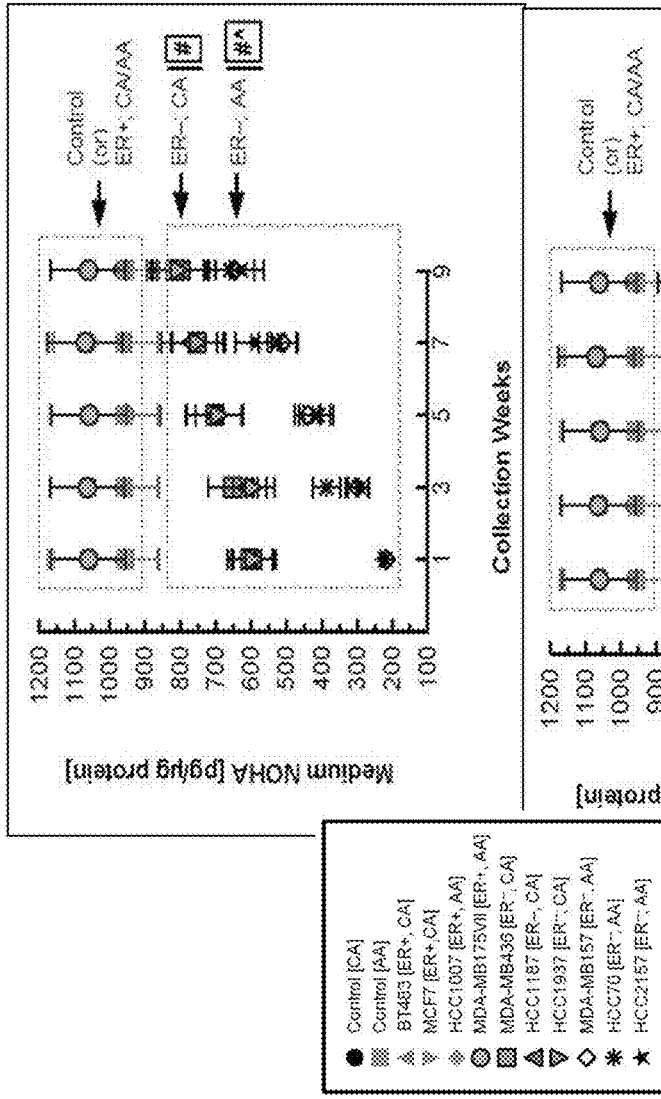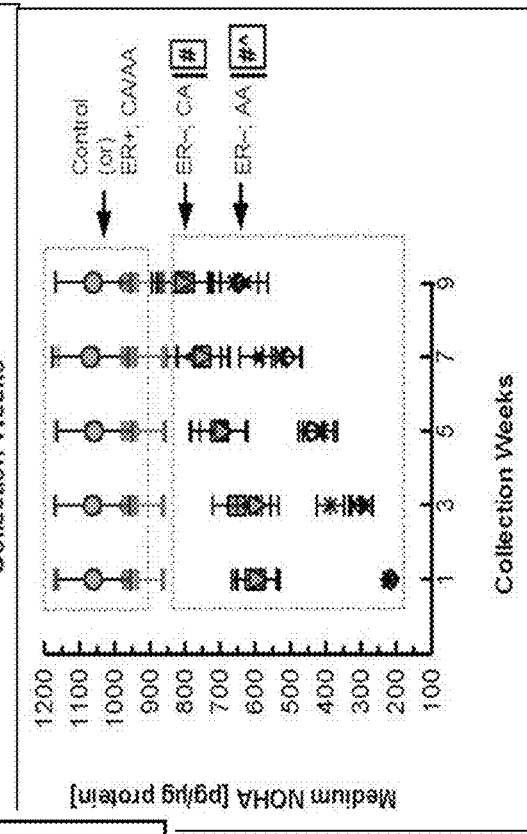
FIG. 8C
FIG. 8D

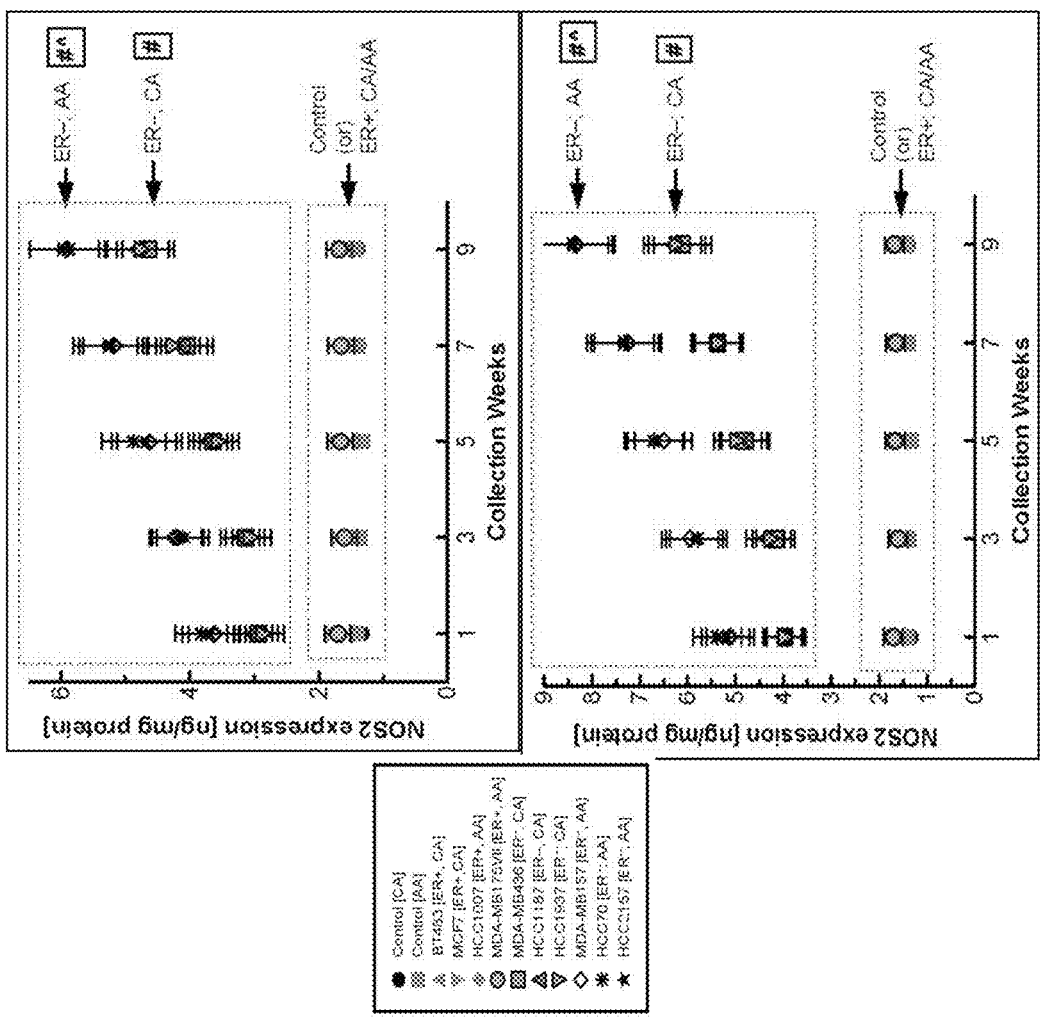

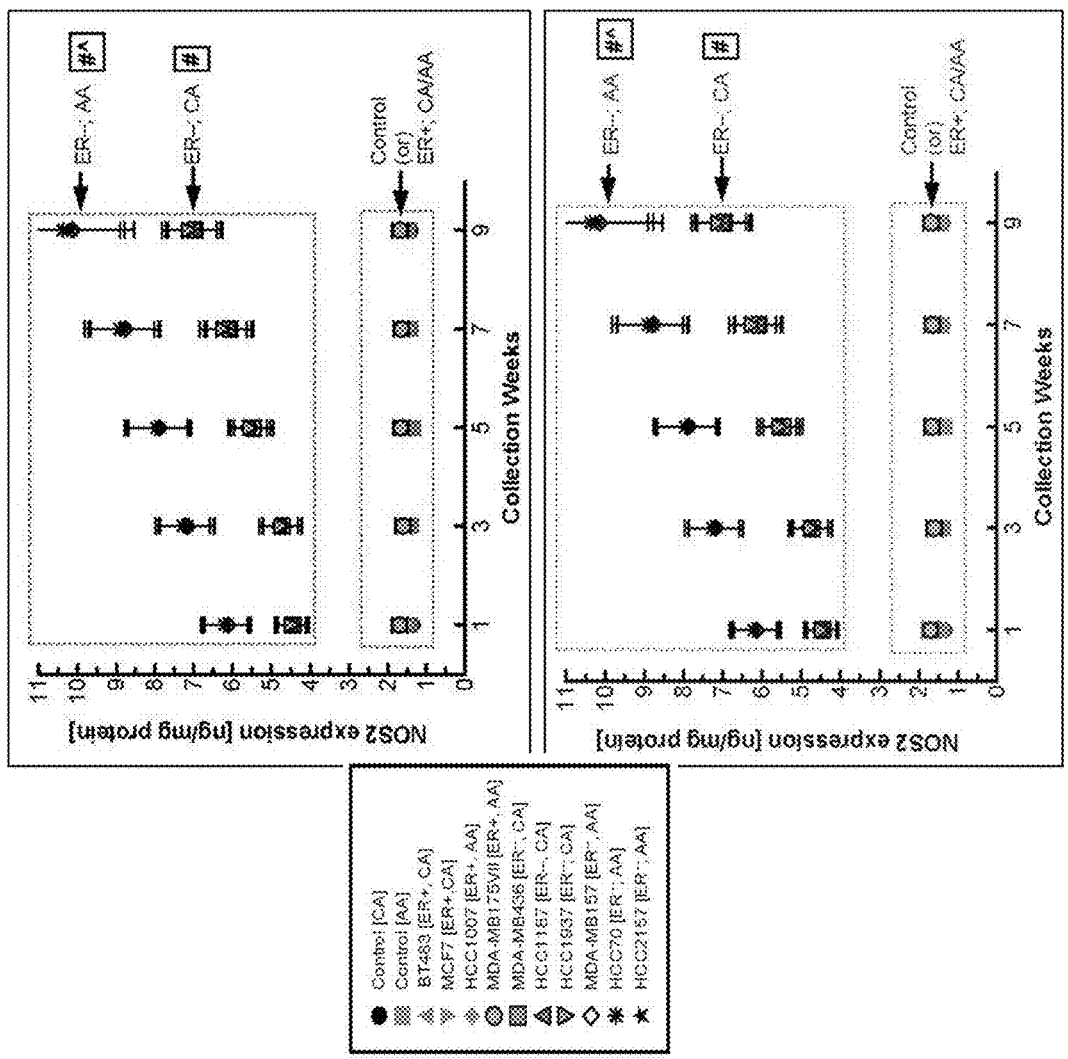

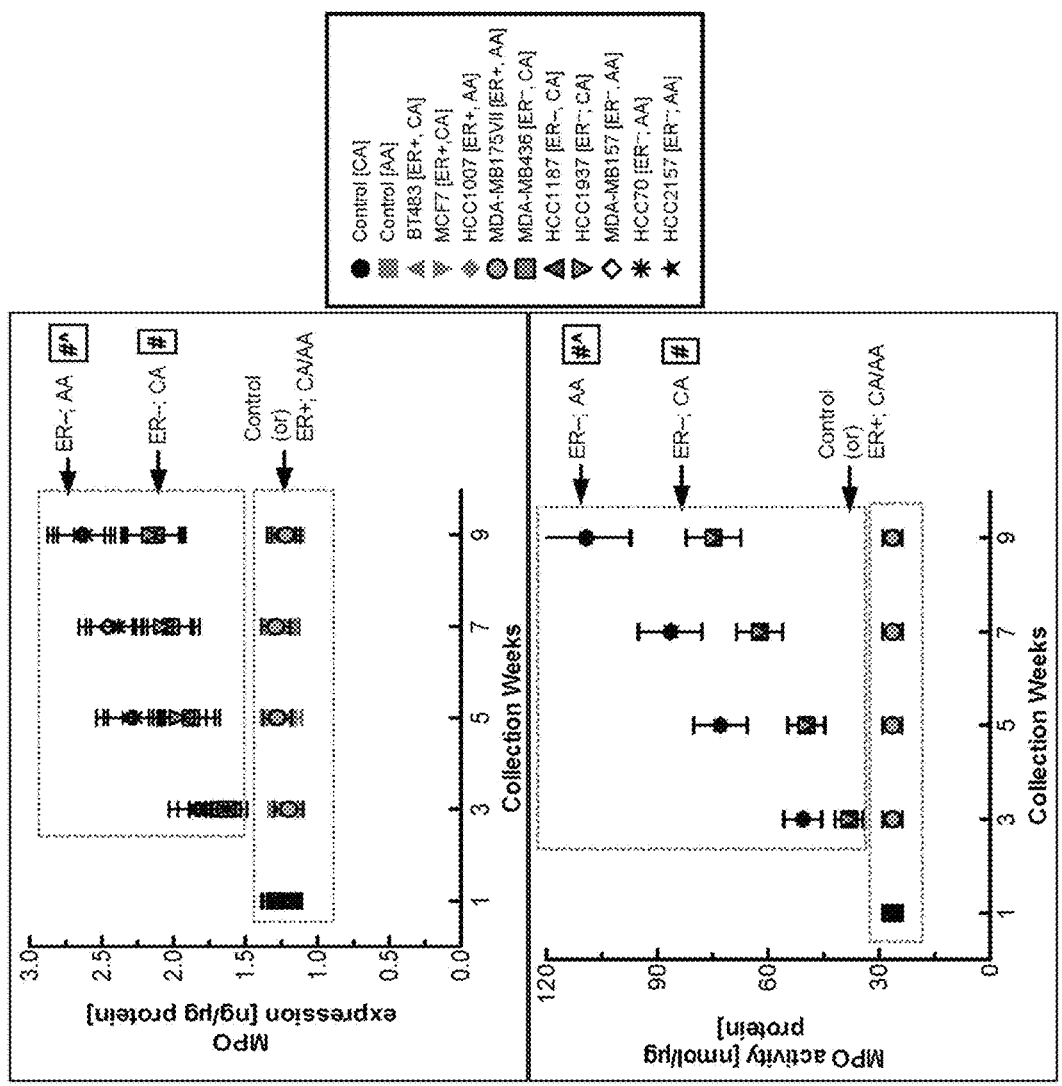

SEQUENCE LISTING

```
<160> NUMBER OF SEQ ID NOS: 1

<210> SEQ ID NO 1
<211> LENGTH: 107
<212> TYPE: PRT
<213> ORGANISM: Artificial Sequence
<220> FEATURE:
<223> OTHER INFORMATION: Synthetic construct

<400> SEQUENCE: 1

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45
```

-continued

```
Asn Gly Val Leu Asn Ser Trp Thr Asp Gln Asp Ser Lys Asp Ser Thr
             50                  55                  60

Tyr Ser Met Ser Ser Thr Leu Thr Leu Thr Lys Asp Glu Tyr Glu Arg
 65                  70                  75                  80

His Asn Ser Tyr Thr Cys Glu Ala Thr His Lys Thr Ser Thr Ser Pro
                 85                  90                  95

Ile Val Lys Ala Ser Phe Asn Arg Asn Glu Cys
                100                 105
```

METHODS AND DIAGNOSTICS FOR CANCER DETECTION AND TREATMENT MONITORING

CROSS-REFERENCE

This application claims priority to and the benefit of U.S. Provisional Application No. 62/232,816, filed on Sep. 25, 2015; U.S. Provisional Application No. 62/295,694, filed on Feb. 16, 2016; and U.S. Provisional Application No. 62/364,539, filed on Jul. 20, 2016. All of these applications are incorporated herein in their entireties.

REFERENCE TO SEQUENCE LISTING

This specification includes a sequence listing provided on a compact disc, submitted herewith, which includes the file entitled 162234-010203_ST25.txt having the following size: 1,3500 bytes which was created Sep. 20, 2016, the contents of which are incorporated by reference herein.

FIELD

The present disclosure provides methods for diagnosing breast cancers (e.g., tumors) and monitoring treatments of breast cancers, as well as compositions and kits that can be used in such methods.

BACKGROUND

Breast cancer is the most common type of cancer and the second most common cancer-related deaths in women in the United States. Among the two major breast cancer subsets of estrogen receptor-negative (ER−) and ER-positive (ER+) tumors, the ER− patients has been recognized as the more aggressive subtype, more difficult to treat, greater ethnic disparity, worse prognosis, and almost twice the risk of mortality than ER+ tumors.

Thus there is an urgent need to identify novel indicators for ER− breast cancer prognosis.

SUMMARY

Methods and diagnostic compositions for monitoring ER− breast cancer are disclosed.

In some aspects, the present disclosure provides an antibody that immunospecifically binds to HOHA, and antibinding fragments thereof. In some embodiments, the antibody comprises the amino acid sequence of SEQ ID NO: 1.

In some aspects, a method of detecting a level of NOHA in a subject is provided, the method comprising obtaining a sample from a subject, and determining a level of NOHA in the sample by contacting the subject sample with a NOHA antibody and detecting binding between NOHA and the NOHA antibody.

In some aspects, a method for detecting ER− breast cancer in a subject is provided, the method comprising obtaining a subject sample from a subject suffering from breast cancer; determining a level of NOHA in the subject sample; and comparing the level of NOHA obtained from the subject sample to the level of NOHA in a control sample, wherein a lower level of NOHA in the subject sample indicates presence of ER− breast cancer in the subject.

In some aspects, a method for detecting a grade of ER− breast cancer in a subject is provided, the method comprising obtaining a subject sample from a subject suffering from breast cancer; determining a level of NOHA in the subject sample; and comparing the level of NOHA obtained from the subject sample to the level of NOHA in a control sample indicative of NOHA levels due to different tumor grades.

In some aspects, a method of monitoring ER− breast cancer in a subject is provided, the method comprising obtaining a subject sample from a subject suffering from breast cancer; determining a level of NOHA in the subject sample; and comparing the level of NOHA obtained from the subject sample to the level of NOHA in a control sample. In some embodiments, the method further comprises diagnosing the subject with ER− breast cancer if the level of NOHA in the subject sample is lower than the level of NOHA in the control sample.

In some aspects, a method for monitoring a treatment regimen for ER− breast cancer is provided, the method comprising determining a level of NOHA in a first sample taken from a subject suffering from ER− breast cancer prior to administering a treatment regimen; determining a level of NOHA in a second sample taken from the subject subsequent to commencement of the treatment regimen; and comparing the level of NOHA in the first sample and the second sample, wherein a higher level of NOHA in the second sample indicates the subject's responsiveness to the treatment regimen.

In some aspects, a method of identifying therapeutic agents that target ER− breast cancer is provided, the method comprising determining a level of NOHA in a first sample taken from a subject suffering from ER− breast cancer prior to administering a therapeutic agent; determining a level of NOHA in a second sample taken from the subject subsequent to administration of the therapeutic agent; and comparing the level of NOHA in the first sample and the second sample, wherein a higher level of NOHA in the second sample indicates an effectiveness of the therapeutic agent in targeting ER− breast cancer in the subject.

In some embodiments, the determining step comprises contacting the subject sample with a NOHA antibody and detecting binding between NOHA and the NOHA antibody. In some embodiments, the determining is achieved with an immunoassay selected from a group consisting of affinity capture assay, immunometric assay, heterogeneous chemiluminscence immunometric assay, homogeneous chemiluminscence immunometric assay, ELISA, western blotting, radioimmunoassay, magnetic immunoassay, real-time immunoquantitative PCR (iqPCR), SERS label free assay and combinations thereof. In some embodiments, the control sample is based on ethnic origin of the subject. In some embodiments, the control sample is based on an expected state of the ER− breast cancer in the subject.

In some aspects, a kit for monitoring ER− breast cancer in a subject is provided, the kit comprising a NOHA antibody that binds to NOHA. In some embodiments, the kit further includes a control sample based on an ethnic origin of a subject to be tested. In some embodiments, the kit further includes a control sample based on an expected state of the ER− breast cancer in a subject to be tested.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 4 illustrates an alignment diagram for an antibody of NOHA.

FIG. 6B presents a plasma NOHA stability analysis based on incubation duration and temperature condition for up to 7 days. n=4.

FIG. 7A represents comparison between Jewish, Asian and Hispanic groups, of ER−/ER+ status. FIG. 7B represents the compilation of all the ethnic disparate groups tested so far (viz., AA, CA, Jewish, Hispanic and Asian origin), of ER−/ER+. All tested plasma samples were derived from patients who have been diagnosed with low-grade, stage 1 breast cancer, and have not undergone chemotherapy.

FIGS. 8A-8D present an analysis of medium NOHA level by ELISA in the presence or absence of inhibitors. FIG. 8A presents a graph showing medium NOHA validation over 9 weeks; FIG. 8B presents a graph showing Arginase inhibitory effect; FIG. 8C presents a graph showing MPO inhibitory effect; FIG. 8D presents a graph showing cytochrome P450 inhibitory effect. #, represents significance from ER+ and control groups; and ^, represents significance from ER−[CA] groups. n=4. P<0.01.

FIGS. 10A-10D present analysis of 3D spheroid NOS2 expression level by ELISA, in the presence or absence of inhibitors. FIG. 10A presents a graph showing NOS2 expression validation over 9 weeks. FIG. 10B presents a graph showing Arginase inhibitory effect; FIG. 10C presents a graph showing MPO inhibitory effect; FIG. 10D presents a graph showing cytochrome P450 inhibitory effect. #, represents significance from ER+ and control groups; and ^, represents significance from ER−[CA] groups. n=4. P<0.01.

FIG. 12A presents a graph showing expression; FIG. 12B presents a graph showing activity. #, represents significance from ER+ and control groups; and ^, represents significance from ER−[CA] groups. n=4. P<0.01

FIG. 13A and FIG. 13B present analysis of MPO; FIG. 13A presents a graph showing expression; FIG. 13B presents a graph showing activity. #, represents significance from ER+ and control groups; and ^, represents significance from ER−[CA] groups. n=4. P<0.01.

Figure 1:
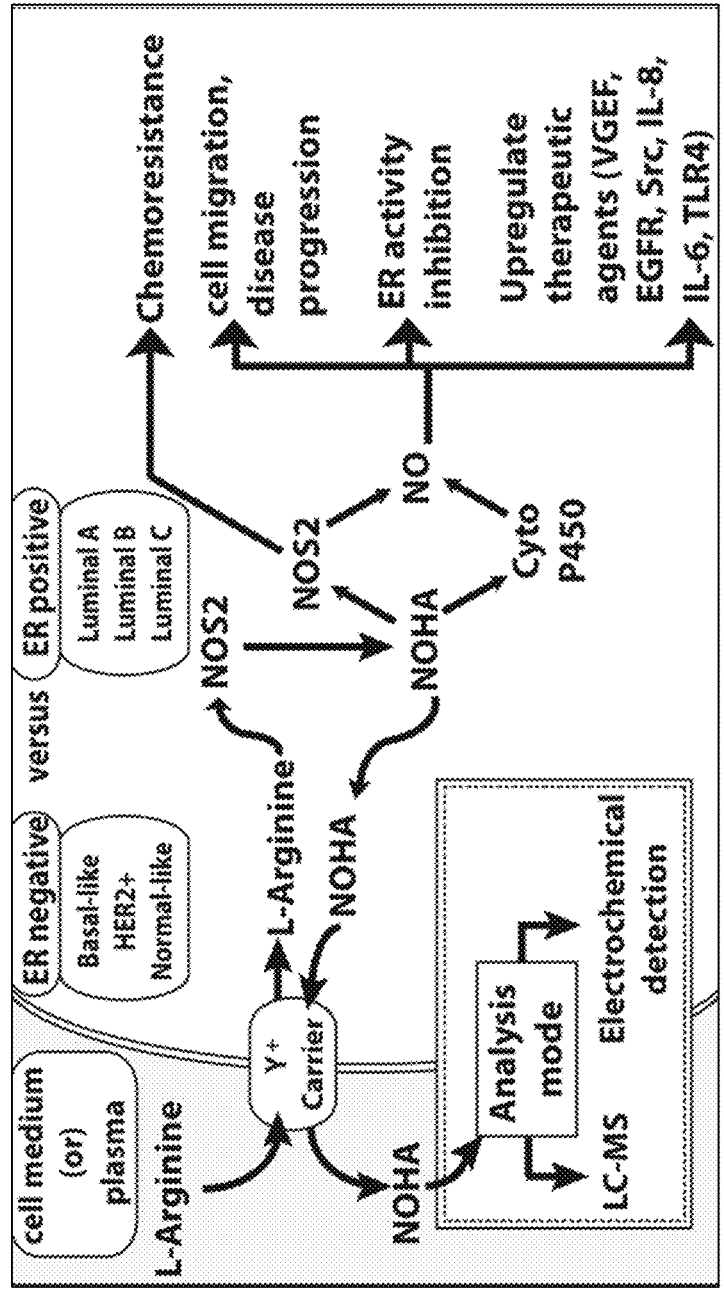
FIG. 1 illustrates the NOHA biochemical pathway.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, the following terms and phrases are intended to have the following meanings:

As used in this specification and the appended claims, the singular forms "a," "an," and "the" include plural references unless the context clearly dictates otherwise. By way of example, "an element" means one element or more than one element. Similarly, references to "the method" includes one or more methods, and/or steps of the type described herein and/or which will become apparent to those persons skilled in the art upon reading this disclosure and so forth.

As used herein, the term "about" means acceptable variations within 20%, more preferably within 10% and most preferably within 5% of the stated value.

As used herein, the term ER− and ER+ refer to two major breast cancer subsets of estrogen receptor-negative (ER−) and ER-positive (ER+) tumors. The ER− patients has been recognized as (a) more aggressive subtype, (b) more difficult to treat, (c) greater ethnic disparity (two fold higher in African American), (d) worse prognosis, (e) almost twice the risk of mortality than ER+ tumors, and (f) ER− leads to triple negative, negative state (e.g., estrogen negative, progesterone negative and HER2 negative).

As used herein the term "Grade 1 tumors" refers to tumors at days 1 and 5, with tumor volume of ≤250 μm, and with cells that look more like healthy cells (is well differentiated or low-grade. A grade 1 tumor (which is an initial stage of cancer development) could be associated with targeted drug/ gene therapy (that focuses on a specific element of a cell, such as molecules or pathways required for cell growth, in order to use them as a target).

As used herein the term "Grade 2 tumors" refers to tumors at days 7 and 10, with tumor volume of ≥400 µm, and with cells that look less like healthy cells (poorly differentiated, intermittent grade of tumor). Grade 2 tumors could be associated with onset of an advanced stage of diseases, where the therapy could involve a combination of targeted therapy, radiation therapy, chemotherapy, and/or surgery.

As used herein the terms "biomarker" or "marker" generally refer to a protein, nucleic acid molecule, clinical indicator, or other analyte that is associated with a disease. In one embodiment, a marker of breast cancer is differentially present in a biological sample obtained from a subject having or at risk of developing breast cancer relative to a reference. A marker is differentially present if the mean or median level of the biomarker present in the sample is statistically different from the level present in a control sample. A control sample level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing breast cancer, for determining the prognosis of the subject, for evaluating therapeutic efficacy, or for selecting a treatment regimen (e.g., selecting that the subject be evaluated and/or treated by a surgeon that specializes in gynecologic oncology).

As used herein, the term NOHA refers to $N^w$-hydroxy-L-Arginine (NOHA). All three isoforms of nitric oxide synthase enzyme (viz., NOS1, NOS2 and NOS3) generate NOHA as a stable intermediate during NO production.

An "antibody," as used herein is a protein consisting of one or more polypeptides comprising binding domains substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin structural unit comprises a tetramer that is composed of two identical pairs of polypeptide chains, each pair having one "light" (about 25 kD) and one "heavy" chain (about 50-70 kD). "VL" and VH" refer to these light and heavy chains respectively.

Antibodies include intact immunoglobulins as well as antigen-binding fragments thereof, which may be produced by digestion with various peptidases, or synthesized de novo either chemically or using recombinant DNA expression technology. Such fragments include, for example, F(ab)2 dimers and Fab monomers. Useful antibodies include single chain antibodies (antibodies that exist as a single polypeptide chain), e.g., single chain Fv antibodies (scFv) in which a VH and a VL chain are joined together (directly or through a peptide linker) to form a continuous polypeptide.

Antibodies also include variants, chimeric antibodies and humanized antibodies. The term "antibody variant" or "variant" as used herein refers to an antibody with single or multiple mutations in the heavy chains and/or light chains. In some embodiments, the mutations exist in the variable region. In some embodiments, the mutations exist in the constant region. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

The term "NOHA antibody" as used herein refers to an antibody that immunospecifically bind to NOHA (e.g., its extracellular domain). The antibody may be an isolated antibody. The NOHA antibody binds to NOHA with a dissociation constant ($K_d$) of $10^{-6}$, $10^{-7}$, $10^{-8}$, $10^{-9}$, $10^{-10}$, $10^{-11}$, $10^{-12}$ M or better. For example, the $K_d$ of an antibody-antigen interaction indicates the concentration of antibody (expressed as molarity) at which 50% of antibody and antigen molecules are bound together at thermodynamic equilibrium. Thus, at a suitable fixed antigen concentration, 50% of a higher (i.e., stronger) affinity antibody will bind antigen molecules at a lower antibody concentration than would be required to achieve the same percent binding with a lower affinity antibody. $K_d$ is also the ratio of the kinetic on and off rates ($k_{on}$ and $k_{off}$); i.e., $K_d = k_{off}/k_{on}$. A lower $K_d$ value indicates a higher (stronger) affinity.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

"Immunospecific" or "immunospecifically" refer to antibodies that bind via domains substantially encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds immunospecifically to a cognate antigen with a Kd with a value of no greater than 50 nM, as measured by a surface plasmon resonance assay or a cell binding assay. The use of such assays is well known in the art.

The term "patient" or "subject" include a human or other mammalian animal that receives either prophylactic or therapeutic treatment.

The terms "treat," "treating," and "treatment," as used herein, refer to therapeutic or preventative measures such as those described herein. The methods of "treatment" employ administration to a patient of a treatment regimen in order to prevent, cure, delay, reduce the severity of, or ameliorate one or more symptoms of the disease or disorder or recurring disease or disorder, or in order to prolong the survival of a patient beyond that expected in the absence of such treatment.

The term "effective amount," as used herein, refers to that amount of an agent, which is sufficient to effect treatment, prognosis or diagnosis of ER– cancer, when administered to a patient. A therapeutically effective amount will vary depending upon the patient and disease condition being treated, the weight and age of the patient, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, as provided herein. Dosing may be, e.g., every week, every 2 weeks, every three weeks, every 4 weeks, every 5 weeks or every 6 weeks. Dosage regimens may be adjusted to provide the optimum therapeutic response. An effective amount is also one in which any toxic or detrimental effects (side effects) of the agent are minimized and/or outweighed by the beneficial effects. Administration may be intravenous at exactly or about 6 mg/kg or 12 mg/kg weekly, or 12 mg/kg or 24 mg/kg biweekly. Additional dosing regimens are described below.

Other terms used in the fields of recombinant nucleic acid technology, microbiology, immunology, antibody engineering and molecular and cell biology as used herein will be generally understood by one of ordinary skill in the applicable arts. For example, conventional techniques may be used for preparing recombinant DNA, performing oligonucleotide synthesis, and practicing tissue culture and transformation (e.g., electroporation, transfection or lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., 2001, Molecular Cloning: A Laboratory Manual, 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "reference" is meant a standard of comparison. For example, the marker level(s) present in a patient sample may be compared to the level of the marker in a corresponding healthy cell or tissue or in a diseased cell or tissue (e.g., a cell or tissue derived from a subject having breast cancer). In particular embodiments, the IGFBP2, IL6, FSH, HE4, CA 125; Transthyretin, Transferrin, TAG-72/CA 72-4 polypeptide level present in a patient sample may be compared to the level of said polypeptide present in a corresponding sample obtained at an earlier time point (i.e., prior to treatment), to a healthy cell or tissue or a neoplastic cell or tissue that lacks a propensity to metastasize. As used herein, the term "sample" includes a biologic sample such as any tissue, cell, fluid, or other material derived from an organism.

By "specifically binds" is meant a compound (e.g., antibody) that recognizes and binds a molecule (e.g., polypeptide), but which does not substantially recognize and bind other molecules in a sample, for example, a biological sample.

As used herein the term "comprising," "having" and "including" and the like are used in reference to compositions, methods, and respective component(s) thereof, that are present in a given embodiment, yet open to the inclusion of one more or more unspecified elements. The term "including" is used herein to mean, and is used interchangeably with, the phrase "including but not limited to."

As used herein the term "consisting essentially of" refers to those elements required for a given embodiment. The term permits the presence of additional elements that do not materially affect the basic and novel or functional characteristic(s) of that embodiment of the invention. The term "consisting of" refers to compositions, methods, and respective components thereof as described herein, which are exclusive of any element not recited in that description of the embodiment.

NOHA Biomarkers and Use Thereof

Among the two major breast cancer subsets of estrogen receptor-negative (ER−) and ER-positive (ER+) tumors, the ER− patients has been recognized as (a) more aggressive subtype, (b) more difficult to treat, (c) greater ethnic disparity (two fold higher in African American), (d) worse prognosis, (e) almost twice the risk of mortality than ER+ tumors, and (f) ER− leads to triple negative state (e.g., estrogen negative, progesterone negative and HER2 negative).

Current indicators/markers for ER− and TNBC breast cancer include carcinoembryonic antigen (CEA) which is used to detect colorectal and breast cancer from blood, both for advanced stage and to check reoccurrence of the tumors. CA15-3/CA27.29 is used in detection of breast cancer from blood as well, for advanced metastatis and to check reoccurrence. No extra-tumoral indicators for early detection are known to currently to be used in detection of ER− cancer.

Inflammation is a major component of the tumor microenvironment and a driving force in cancer initiation, promotion and progression. The inflammation-associated enzyme, inducible nitric oxide synthase (NOS2), has recently emerged as a candidate oncogene in ER− breast cancer. Up-regulation in NOS2 expression has been associated with disease aggressiveness and poor survival. Although observations implicate NOS2 as an attractive therapeutic target, the roles of NOS2 up-regulation in ER− cancer progression among ethnically diverse groups is currently unclear; and current markers that could directly correlate with NOS2 (viz., epidermal growth factor receptor; vascular endothelial growth factor; and poly-adenosine-di-phosphate ribose polymerase inhibitors) show inconsistent results in ethnically distinctive populations.

NOS2 feed forward regulation is a primary indicator of inflammation, is upstream to current breast cancer markers (VEGF, Src, EGFR, etc), and shows aberrant expression in many solid tumors including breast, colon cancer, and also in melanoma. The drawback is that NOS2 is not extratumoral and no ethnic specificity has been attempted.

All three isoforms of nitric oxide synthase enzyme (viz., NOS1, NOS2 and NOS3) generates $N^w$-hydroxy-L-Arginine (NOHA) as a stable intermediate during NO production. Only cells expressing the calcium independent NOS2 (viz., EMT-6 mammary adenocarcinoma cells, RAW 264.7 macrophages) have been shown to liberate substantial amounts of NOHA to accumulate in culture medium and in circulating blood. No other sources other than the three nitric oxide synthase isozymes appear to generate NOHA.

As seen in FIG. 1, NOHA is a stable intermediate of L-arginine utilization by NOS. While all three isozymes of NOS (NOS1, NOS2, and NOS3) produce NOHA, only Ca2+ independent NOS2 can liberate NOHA into the matrix. Since the liberated NOHA has to compete with L-arginine for the same amino acid carrier (y+ system) for their cellular re-absorption, and since NOS exhibits a two-fold higher Km requirement for NOHA than L-arginine, cellular re-uptake of NOHA and its metabolism will only be possible when the extracellular and intracellular L-arginine concentrations fall drastically below a critical threshold limit.

According to some aspects of the present disclosure, NOHA can be used as a sensitive and reliable biomarker for ER− breast cancer early prognosis. In some embodiments, the methods of the present disclosure test for extracellular or circulating NOHA level.

In some embodiments, a reduction in the NOHA levels in a sample as compared to a control sample (a sample from a healthy subject) indicates a presence of ER− breast cancer. In some embodiments, the NOHA reduction has to be statistically significant (for example, p-value of less than 0.01). In some embodiment, the change in the NOHA level may simply be a general trend of reduction in the NOHA level.

In some embodiments, such prognosis may be made based on ethnic orientation, that is, NOHA has been shown to exhibit ethnic specificity in patients. In some embodiments, a greater reduction in the NOHA levels can be observed in African American patients than in Caucasian patients.

Understanding the ethnic specificity of NOHA in ER− breast cancer is desirable as there is greater ethnic disparity among ER− breast tumor with 2-3 fold higher instances among African American populations, with earlier onset than other ethnic origin. In addition to showing ethnic disparity in NOHA reduction between ER− CA versus ER− AA, when other ethnic races of Jewish, Asian and Hispanic origins were accessed for NOHA reduction based on ER expression, a significant reduction in NOHA was identified for ER− Jewish, Asian and Hispanic population compared to Healthy or ER+ groups. The level of NOHA reduction in ER− Jewish groups was ≥24% more than those of ER− Asian or ER− Hispanic origin. However, the greatest NOHA reduction was seen with ER− AA groups. The level of NOHA reduction between ER− Asian, ER− Hispanic, and ER− CA groups were comparable to one another. Plasma NOHA for ER+ and healthy groups was comparable to one another with no ethnic-specific difference. In some embodiments, the clinical relevance of NOHA as a selective prognostic marker for ER− breast cancer patients, with favorable ethnic selectivity, may be utilized to make the present methods of detection and monitoring ER− breast cancer more precise.

In some embodiments, the close correlation of NOHA reduction based on ethnic orientation can be utilized for it to sensitively detect a heterogeneous disease such as cancer. In some embodiments, NOHA can be detected for use as a predictive indicator in determining whether an individual would be likely to develop aggressive cancer, even before the actual cyst or tumor development. Based on ethnic orientation, the aggressive cancer subtypes such as estrogen negative and triple negative breast cancer can occur more frequently in much younger individuals (such as in African Americans, where such aggressive breast cancer can occur with individuals in their mid 20's), way ahead of their scheduled screening (which would be in the 40's). In some embodiments, the NOHA levels can be used to screen for the presence of such cancers. In some embodiments, since aberrant changes with the enzyme responsible for NOHA production are seen with other solid tumors (viz., lung, colon, prostrate and melanoma), the predictive response of NOHA (seen here with breast cancer; as an immediate outcome) can be used with other solid tumors (viz., as extended outcome), in similar fashion as outlined above.

In some embodiments, monitoring the NOHA levels can be used to determine a severity of tumor. For example, a reduction in the NOHA levels can indicate a change in tumor severity from Grade 1 tumor to Grade 2 tumor. However, an increase in the levels of NOHA may indicate an improvement in the patient condition. In some embodiments, the levels of extracellular NOHA are detected and monitored. Tumor grades can usually be determined by the Nottingham grading system (viz., low-grade or grade 1, where cancer cells that resemble normal cells and aren't growing rapidly; intermediate-grade or grade 2, where cells don't look like normal cells and are growing faster; and, high/advanced-grade or grade 3, where cancer cells look abnormal and may grow or spread more aggressively). In some embodiments, the NOHA level can be measured for prognosis on disease aggressiveness. In some embodiments, the levels of NOHA may be used for planning tumor prognosis and disease treatment, and to avoid the metastasis ambiguity (that is associated while staging such aggressive tumor). In some embodiments, the methods of the present disclosure may include monitoring the progressive change (increase or decrease) in the volume of NOHA to determine tumor volume or grade.

For example, a NOHA reduction by at least 0.85 fold in ER− CA group versus 1.9-fold reduction in ER− AA group will be representative of grade 1 tumor, where cancer cells would resemble normal cells and aren't growing rapidly. However, a NOHA reduction in ER− CA, by at least 3.9 fold versus in ER− AA, by 9.4 fold is indicative of grade 3/advance tumors, where cancer cells look abnormal and may grow or spread more aggressively. An intermediate NOHA value, between those of grade 1 and 3 range, would be representative of a grade 2 tumor, where cells don't look like normal cells and are growing faster, but have not started to spread.

In some embodiments, the present disclosure provides a method of detecting a level of NOHA in a subject, the method comprising obtaining a sample from a subject, and detecting a level of NOHA in the sample. The level of NOHA in the sample from the subject can then be compared to the level of NOHA in a control sample, which can be taken from a healthy subject or can be a previously-obtained sample from the same subject. The level of NOHA can be detected by a variety of methods known in the art, as described in more detail below. For example, in some embodiments, the level of NOHA can be detected by contacting the sample with a NOHA antibody and detecting binding between NOHA and the NOHA antibody, but other methods can also be used.

In some embodiments, the present disclosure provides a method for detecting ER− breast cancer in a subject, the method comprising obtaining a subject sample from a subject suffering from breast cancer; determining a level of NOHA in the subject sample; and comparing the level of NOHA obtained from the subject sample to the level of NOHA in a control sample, wherein a lower level of NOHA in the subject sample indicates presence of ER− breast cancer in the subject.

In some embodiments, methods for determining the course of ER− breast cancer in a subject are provided. Disease course refers to changes in disease status over time, including disease progression (worsening) and disease regression (improvement). Over time, the amounts or relative amounts (e.g., the pattern) of the biomarkers change. Accordingly, the present methods may involve measuring the level of NOHA in a subject at least two different time points, e.g., a first time and a second time, and comparing the change in amounts, if any. The course of disease (e.g., during treatment) is determined based on these comparisons.

In some embodiments, the present disclosure provides a method for monitoring a treatment regimen for ER− breast cancer, the method comprising determining a level of NOHA in a first sample taken from a subject suffering from ER− breast cancer prior to administering a treatment regimen; determining a level of NOHA in a second sample taken from the subject subsequent to commencement of the treatment regimen; and comparing the level of NOHA in the first sample and the second sample, wherein a higher level of NOHA in the second sample indicates the subject's responsiveness to the treatment regimen. For example, an improvement in NOHA after a specific therapeutic treatment (viz., chemotherapy), by at least half-fold, would be indicative of a positive effect to the treatment, while no change in NOHA (or a potential decrease) in comparison to NOHA level prior to such treatment would be representation of an ineffective treatment (or a negative treatment outcome).

In some embodiments, the present disclosure provides a method of identifying therapeutic agents that target ER− breast cancer, the method comprising determining a level of NOHA in a first sample taken from a subject suffering from ER− breast cancer prior to administering a therapeutic agent; determining a level of NOHA in a second sample taken from the subject subsequent to administration of the therapeutic agent; and comparing the level of NOHA in the first sample and the second sample, wherein a higher level of NOHA in the second sample indicates an effectiveness of the therapeutic agent in targeting ER− breast cancer in the subject.

In some embodiments, a method for prognosis of a tumor comprises monitoring NOHA that is liberated from cells expressing NOS2. In some embodiments, monitoring further comprises generating a specific index for tumor prognosis. The index may include expected levels of NOHA in a healthy individual or an individual having a tumor of a specific grade. The data in the index may also include values averaged for all ethnicities, or different values for individuals of different ethnicities. For example, when compared to healthy individual NOHA level, a reduction by at least half-fold can be indicative of an individual, irrespective of their ethnic origin to be more likely to develop aggressive breast cancer such as ER− breast cancer.

In some embodiments, monitoring NOHA further comprises generating a specific and more reliable index for tumor prognosis in racially diverse groups. In some embodiments, the racially diverse groups are African American and Caucasians population, wherein each racially diverse group may have different indexes for tumor prognosis. In some embodiments, the racially diverse groups may be Asians, Hispanics or Mongolians. The index may include the values of NOHA levels expected in individuals of different ethnic backgrounds. In some embodiments, the index may include a correlation between a change in the level of NOHA and status of cancer or prognosis of cancer for specific ethnic groups. Based on ethnic orientation, a 1 fold decrease in NOHA from those of healthy individuals would suggest ER⁻ breast cancer onset in those individuals of Caucasian origin; wherein they would have been considered to have developed a low grade tumor, and are at their early stages with such cancer. Such a Caucasian patient would be prescribed for additional diagnostic screening (viz., morphological imaging such as mammogram, immunohistochemistry analysis, genetic screening for additional biomarkers related with such aggressive cancer, etc), followed with possible consultation for a treatment regimen. However, for African American patient with only a 1 fold NOHA reduction would be considered as an indication that the patient would be more likely (or has a potential) to develop an aggressive tumor like ER⁻ breast cancer in the near future, and would be advised to self-monitor (using a NOHA home-kit assay, daily for 2 weeks), or be screened at a diagnostic center twice a week (for 2 weeks), along with potential genetic counseling to better understand the potential risk of developing such aggressive tumor, prior to prescribing additional screening or diagnostic procedures. Thus, the level of NOHA reduction based on ethnicity would allow personalizing cancer care and provides better monitoring of the treatment outcome measurement.

In some embodiments, monitoring extracellular and intracellular concentration of L-arginine below a critical threshold is a proxy for monitoring NOHA. High NOS2 expression and nitric oxide production are indicators for poor ER- breast cancer survival. L-arginine, is the substrate for NOS2 mediated NOHA and nitric oxide production. A high NOS2 expression, would favor increased L-arginine uptake, (for cellular nitric oxide production). This would thus result in a higher intracellular L-Arginine concentration, with a reduction in the extracellular L-Arginine and NOHA level.

In some embodiments, monitoring NOHA levels further comprises defining a predictive response between ER- tumor ethnic groups. In some embodiments, the predictive response further comprises a better therapy outcome measurement. In some embodiments the predictive response further comprises preventing unnecessary exposure of unresponsive patients to ineffective therapy.

In some embodiments, monitoring NOHA allows for predicting ethnic-specific response in other solid tumor or cancer prognosis. In some embodiments, the tumor is breast tumor. In some embodiments, the tumor may be ovarian, brain, prostrate, lung, liver, pancreatic, colon, rectal, and kidney/renal. In some embodiments the cancer may be a melanoma, sarcoma or a lymphoma.

In some embodiments, the monitoring further comprises a method for measuring therapy outcome, wherein NOHA levels are measured to help in better understanding whether a particular therapy is beneficial or not and thus help in better individualization of therapy. In some embodiments, the monitoring further comprises determining a chemoresistance pattern for the patient. In some embodiments, the monitoring further comprises determining tumor migration and tumor response under environmental stimuli.

Detection of NOHA

The level of NOHA biomarker may be detected in a biological sample of the subject (e.g., tissue, fluid). Suitable samples, include, but are not limited to, blood, blood serum, plasma, saliva, urine, ascites, cyst fluid, a homogenized tissue sample (e.g., a tissue sample obtained by biopsy), a cell isolated from a patient sample, and similar sample of tissue or bodily fluid.

NOHA can be detected by any suitable method. The methods described herein can be used individually or in combination for a more accurate detection of the biomarkers (e.g., biochip in combination with mass spectrometry, immunoassay in combination with mass spectrometry, and the like).

Detection methods that can be employed for detection of NOHA include, but are not limited to, optical methods, electrochemical methods (voltametry and amperometry techniques), atomic force microscopy, and radio frequency methods, e.g., multipolar resonance spectroscopy.

In some embodiments, the levels of NOHA can be measured by immunoassay. Immunoassay typically utilizes an antibody (or other agent that specifically binds the marker) to detect the presence or level of a biomarker in a sample. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

Suitable immunoassay detection methods include, for example, Western blot, sandwich immunoassays including ELISA and other enzyme immunoassays, fluorescence-based immunoassays, and chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

In some embodiments, the level of NOHA can be detected by mass spectrometry (MS). Mass spectrometry is a well-known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer and hybrids of these. The method may be performed in an automated (Villanueva, et al., Nature Protocols (2006) 1(2):880-891) or semi-automated format. This can be accomplished, for example with the mass spectrometer operably linked to a liquid chromatography device (LC-MS/MS or LC-MS) or gas chromatography device (GC-MS or GC-MS/MS).

In some embodiments, NOHA will be monitored by ELISA. In some embodiments, NOHA can be determined by an LC-MS method or via an electrochemical detection method using micro-electrodes (either static-cell or flow-cell electrodes). In some embodiments, the monitoring may comprise colorimetric, chemiluminescence or fluorometric assays. However, as noted above, other known methods or techniques can be used to detect the level of NOHA.

Antibodies for ELISA

In some embodiments, the present disclosure provides NOHA antibodies that can be used for ELISA assays. Various methods can be used to prepare such NOHA antibodies. The steps for making custom antibodies for ELISA assays include conjugating a carrier protein and small molecule where a small molecule (such as NOHA) is not sufficiently complex by itself to induce an immune response or be processed in a manner that elicits production of specific antibodies. For antibody production to be successful with small antigens, they must be chemically conjugated with immunogenic carrier proteins (such as keyhole limpet hemocyanin; KLH). Adjuvants can be mixed and injected with an immunogen to increase the intensity of the immune response. The method also includes a step of immunization. For example, several (for example, 5) mice (balb/c) can be immunized for serum positive to NOHA. The best animals can be taken to the next stage of fusion. ELISA evaluation of titer can be performed prior to selection for fusion. Approximately 3-4 mg of protein immunogen (or) 3 mg of conjugated peptide and 0.5 mg of free peptide may be required for this stage. The method may also include a step of fusion. For example, once an acceptable titer is obtained, hybridoma fusion can be done using splenocytes from mouse with the best titer and myeloma cells. Supernatant from the growing hybridoma wells can be screened by ELISA. Next, desirable parental clones, once identified, are subjected to sub-cloning. For example, best clones can be sub-cloned by limiting dilution. The selected cells can be sub-cultured in vitro and isotyped. Hybridoma cells can be cryopreserved.

In some embodiments, a NOHA antibody comprises a sequence:

```
                                         (SEQ ID NO: 1)
ADAAPTVSIFPPSSEQLTSGGASVVCFLNNFYPKDINVKWKIDG

SERQNGVLNSWTDQDSKDSTYSMSSTLTLTKDEYERHNSYTCEA

THKTSTSPIVKASFNRNEC.
```

One of ordinary skill in the art would be able to ascertain the CDRs by analyzing SEQ ID NO: 1, e.g., based on the Kabat or Chothia definition. Thus, antibodies, or antigen-binding fragments thereof, having the CDRs of SEQ ID NO: 1, e.g., CDR-L1, CDR-L2, CDR-L3, CDR-H1, CDR-H2 and CDR-H3, are also part of the present disclosure.

In some embodiments, a NOHA antibody comprises a sequence that has at least about 50% identity, at least about 60%, at least about 70%, at least about 80%, at least about 90%, at least about 95%, at least about 98% identity or at least about 99% identity to SEQ ID NO: 1. In some embodiments, a NOHA antibody comprises a sequence that has at least about 50% identity, at least about 60%, at least about 70%, at least about 80%, at least about 90%, at least about 95%, at least about 98% identity or at least about 99% identity to SEQ ID NO: 1 and comprises a sequence KTSTS (amino acids 91-95 of SEQ ID NO: 1). In some embodiments, a NOHA antibody comprises a sequence KTSTS (amino acids 91-95 of SEQ ID NO: 1. In some embodiments, a NOHA antibody comprises a sequence of amino acids 85-95 of SEQ ID NO: 1. In some embodiments, a NOHA antibody comprises a sequence of amino acids 80-95 of SEQ ID NO: 1. In some embodiments, a NOHA antibody comprises a sequence of amino acids 75-95 of SEQ ID NO: 1. In some embodiments, a NOHA antibody comprises a sequence of amino acids 70-95 of SEQ ID NO: 1. In some embodiments, a NOHA antibody comprises a sequence of amino acids 65-95 of SEQ ID NO: 1.

In some embodiments, a NOHA antibody comprises a sequence of amino acids 91-100 of SEQ ID NO: 1. In some embodiments, a NOHA antibody comprises a sequence of amino acids 90-100 of SEQ ID NO: 1. In some embodiments, a NOHA antibody comprises a sequence of amino acids 85-100 of SEQ ID NO: 1. In some embodiments, a NOHA antibody comprises a sequence of amino acids 80-100 of SEQ ID NO: 1. In some embodiments, a NOHA antibody comprises a sequence of amino acids 75-100 of SEQ ID NO: 1. In some embodiments, a NOHA antibody comprises a sequence of amino acids 70-100 of SEQ ID NO: 1. In some embodiments, a NOHA antibody comprises a sequence of amino acids 65-100 of SEQ ID NO: 1.

In some embodiments, a NOHA antibody comprises a sequence of amino acids 91-105 of SEQ ID NO: 1. In some embodiments, a NOHA antibody comprises a sequence of amino acids 90-105 of SEQ ID NO: 1. In some embodiments, a NOHA antibody comprises a sequence of amino acids 85-105 of SEQ ID NO: 1. In some embodiments, a NOHA antibody comprises a sequence of amino acids 80-105 of SEQ ID NO: 1. In some embodiments, a NOHA antibody comprises a sequence of amino acids 75-105 of SEQ ID NO: 1. In some embodiments, a NOHA antibody comprises a sequence of amino acids 70-105 of SEQ ID NO: 1. In some embodiments, a NOHA antibody comprises a sequence of amino acids 65-105 of SEQ ID NO: 1.

Compositions and Kits

Compositions and kits for detecting NOHA and thus, diagnosing or monitoring ER− breast cancer are also provided. In some embodiments, a composition is provided that includes an agent that recognizes NOHA. In some embodiments, a kit is provided that includes an agent that recognizes NOHA. In some embodiments, the compositions and kits of the present disclosure can include one or more NOHA antibodies, or antigen binding fragment thereof, for use in connection with an immunoassay such as immunohistochemistry or ELISA or Western blot.

Alternatively, the kit can include specific primers and/or probes for use in connection with qRT-PCR (e.g., using primers of 10-30 bp designed to target SEQ ID NO.:1) or Northern blot (e.g., using probes of 30-300 bp designed to target SEQ ID NO.:1). The kit can also include a microarray for detecting Procr mRNA or protein level where Procr gene or a fragment thereof, or anti-PROCR antibody or an antigen binding fragment thereof, can be attached to the microarray.

In some embodiments, the kit comprises a solid support, such as a chip, a microtiter plate or a bead or resin having capture reagents attached thereon, wherein the capture reagents bind N. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagents.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for use in any of the methods described herein. In embodiments, the instructions provide suitable operational parameters in the form of a label or separate insert. For example, the instructions may inform a consumer about how to collect the sample, how to wash the probe or the particular biomarkers to be detected.

A control sample can additionally be included in the kit, wherein a difference in the test sample compared to the control sample can indicates a status of ER− breast cancer. The change can be more than about 10%, more than about 20%, more than about 30%, more than about 50%, more than about 60%, more than about 80%, more than about 100%, or more, or any number therebetween. The control sample may be indicative of a healthy individual, or an individual having ER− tumor of one or more grades and severities. In some embodiments, the control may include controls for different ethnic backgrounds.

The compositions and methods of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1: Changes in NOHA Levels

Figure 2:
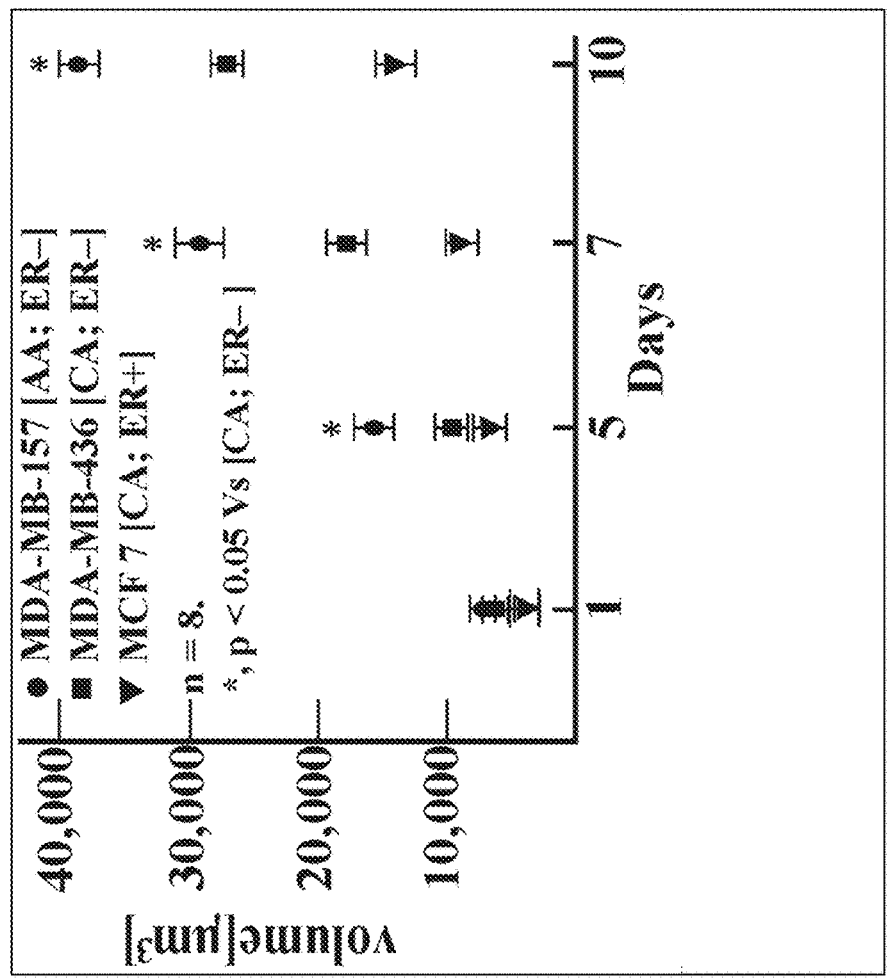
FIG. 2 illustrates a graph of volume assessment of NOHA over time in various cell types.

Tests were performed using a 3D spheroid cell model. 3D models provide an in vitro condition closely mimicking the tumor micro-environment that would otherwise be difficult to achieve via traditional cell mono-layer and in xenograph or severely immune-deficient animal models. Further, 3D models allow for NOHA monitoring during tumor growth, are easy to develop, superior cytoarchitecture, and closely reflects the human tumor biology. FIG. 2 illustrates NOHA volume assessment results obtained with cells of 3 types: ER+, Caucasia [CA] origin (MCF7); ER−, African American [AA] origin (MDA-MB-157) and ER−, CA (MDA-MB-436).

Table 1 below presents relation of NOHA levels to tumor grade, wherein (*) represents significance versus ER+ and control, and (#) represents significance for ER− cell types of AA versus CA. n=8, p<0.01. Grade 1 tumor refers to a tumor with cells that look more like healthy cells (viz., is well differentiated or low-grade); and Grade 2 tumor refers to a tumor with cells that look less like healthy cells (viz., poorly differentiated, intermittent grade of tumor)

TABLE 1

| Tumor grade | Days | 3D spheroids measured for NOHA (nM) | | | |
|---|---|---|---|---|---|
| | | Control [AA/CA] | MDA-MB-157 [AA; ER−] | MDA-MB-436 [CA; ER−] | MCF7 [CA; ER+] |
| Grade 1 | 1 | 66.4 ± 7.1 | 36.9 ± 4.1*# | 44.4 ± 5.1*# | 56.2 ± 5.8 |
| | 5 | 67.1 ± 6.2 | 31.3 ± 3.8*# | 39.6 ± 4.2*# | 54.6 ± 5.2 |
| Grade 2 | 7 | 62.4 ± 6.8 | 16.2 ± 2.1*# | 24.6 ± 2.6*# | 53.7 ± 5.1 |
| | 10 | 63.3 ± 6.7 | 13.8 ± 1.4*# | 23.4 ± 1.9*# | 50.3 ± 6.1 |

Table 2 demonstrates 2D cell model pilot data. (*) represents significance versus ER+ and control, and (#) represents significance for cell types of AA versus CA. n=5, p<0.01

TABLE 2

| Cell type | NOHA (nM) |
|---|---|
| Control [AA/CA] | 382.5 ± 38.1 |
| MDA-MB-157 [AA; ER−] | 171.8 ± 19.3*# |

TABLE 2-continued

| Cell type | NOHA (nM) |
|---|---|
| MDA-MB-436 [CA; ER−] | 216.4 ± 22.7* |
| MCF7 [CA; ER+] | 365.6 ± 39.1 |
| HCC 1007 [AA; ER+] | 376.2 ± 38.2 |

In reference to Table 3, NOHA demonstrates ethnic specificity as a diagnostic biomarker. In some embodiments, there is a ≥59% reduction for NOHA in extracellular medium of ER− cancers. In some embodiments, there is ≥31% decrease in NOHA concentration in cells from African American (AA) versus Caucasian (CA). Table 3 presents a comparison of metabolite in ER+ versus ER− breast 3D spheroid tumor cells types.

TABLE 3

| Cell type [Ethnicity] | Extracellular NOHA (nM) | NOS2 expression (ng/mg protein) | Total nitrite (pmol/μg protein) |
|---|---|---|---|
| ER+ breast tumor cells | | | |
| BT483 [CA] | 53.4 ± 5.3 | 1.54 ± 0.1 | 1.24 ± 0.1 |
| MCF7 [CA] | 53.7 ± 5.1 | 1.59 ± 0.1 | 1.15 ± 0.1 |
| HCC1007 [AA] | 54.8 ± 5.4 | 1.67 ± 0.2 | 1.29 ± 0.1 |
| MDA-MB175VII [AA] | 55.1 ± 5.7 | 1.71 ± 0.2 | 1.19 ± 0.1 |
| ER− breast tumor cells | | | |
| MDA-MB436 [CA] | 24.6 ± 2.6* | 2.94 ± 0.3* | 2.34 ± 0.2* |
| HCC1187 [CA] | 25.1 ± 2.8* | 3.02 ± 0.2* | 2.54 ± 0.3* |
| HCC1937 [CA] | 23.9 ± 2.7* | 2.84 ± 0.3* | 2.48 ± 0.2* |
| MDA-MB157 [AA] | 16.2 ± 2.1*# | 3.62 ± 0.4*# | 2.92 ± 0.2*# |
| HCC70 [AA] | 16.8 ± 2.5*# | 3.82 ± 0.4*# | 3.12 ± 0.3*# |
| HCC2157 [AA] | 15.9 ± 2.8*# | 3.71 ± 0.4*# | 3.19 ± 0.3*# |
| Control cells | | | |
| Mammary epithelial cells | 63.2 ± 6.4 | 1.34 ± 0.1 | 0.98 ± 0.1 |
| Mammary epithelial cells | 61.3 ± 7.2 | 1.44 ± 0.1 | 1.04 ± 0.1 |

Example 2: Translatability of In Vitro Findings in Patient Blood Samples

Blood plasma samples from ethnically disparate patients of African American (AA), and Caucasian origin (CA), who were identified to be healthy (viz., control group), estrogen-receptor-negative (ER−), or estrogen-receptor-positive (ER+) were monitored for NOHA by LC-MS assay to determine the translatability of prior in vitro findings in clinical samples.

Figure 3:
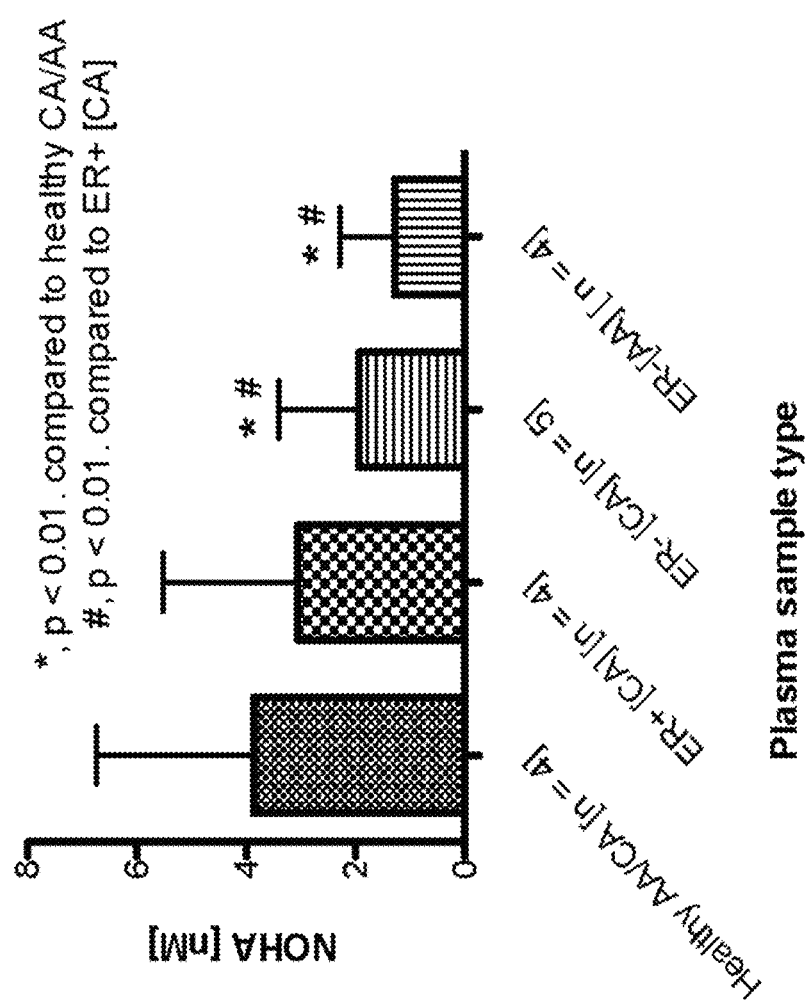
FIG. 3 is a graph demonstrating NOHA measurement in ER+/ER− breast cancer patient samples of African American [AA] and Caucasia [CA] origin.

In reference to FIG. 3, the clinical samples showed translatable results with 38%, and 58% NOHA reduction in ER− groups of CA and AA origin respectively, when compared with ER+ groups of CA origin. As seen in FIG. 3, a greater NOHA reduction of 49% and 65% was observed with ER− groups of CA and AA origin respectively, when compared with healthy control groups of AA or CA origin. The present data thus confirms the clinical relevance of NOHA as a selective prognostic marker for ER− breast cancer patients.

Example 3: NOHA Stability Analysis Over Temperature

Extracellular matrix medium from cancerous and non-cancerous 3D spheroid (viz., 300 μl/spheroid cell line), that was collected on day 7 after spheroid formation were divided in to six (6) equal volumes of 50 μl each. Each of the 50-μl fractions/spheroid cell lines were incubated at −80° C., −20° C., 4° C., 25° C., 37° C. and 42° C. for 1, 3, 5, 7, 10, 12, and 14 days. At the end of the incubation, NOHA level was monitored by LC-MS (Tables 4.1-4.6).

Extracellular matrix medium incubated at lower temperatures (at 4° C., −20° C., and −80° C.) showed no significant degradation or reduction in NOHA level after 14-day incubation at those temperatures (Tables 4.3, 4.5, and 4.6). While medium samples incubated at 25° C. showed stable NOHA monitoring level until 12 days of storage at that temperature (Table 4.1), medium samples stored at 37° C. showed stable NOHA monitoring for only up to 7 days (Table 4.2). Those medium samples that were incubated at higher temperature of 42° C. suffered the most with NOHA stability, which lasted for only 3 days (Table 4.4).

Tables 4.1-4.6: NOHA measurements after incubation at various temperatures

TABLE 4.1

| sample type | | Temperature room temp: 25° C. | | | | | |
|---|---|---|---|---|---|---|---|
| | | NOHA concentration (nM) in Days after incubation | | | | | |
| Control | ethnicity | 1 | 3 | 7 | 10 | 12 | 14 |
| mammary cells | CA | 61.3 ± 7.1 | 60.9 ± 6.8 | 61.1 ± 6.8 | 60.3 ± 7.2 | 61.1 ± 7.1 | 50.3 ± 7.2* |
| mammary cells ER+ | AA | 60.4 ± 6.8 | 60.8 ± 7.1 | 60.0 ± 6.1 | 59.9 ± 6.3 | 59.4 ± 6.2 | 49.9 ± 6.3* |
| BT483 | CA | 53.3 ± 6.1 | 53.8 ± 6.3 | 53.4 ± 6.2 | 52.9 ± 6.6 | 53.6 ± 6.4 | 42.9 ± 6.6* |
| MCF7 | CA | 55.2 ± 5.8 | 55.5 ± 5.4 | 55.8 ± 5.1 | 54.9 ± 5.1 | 55.2 ± 5.2 | 44.9 ± 5.1* |
| HCC1007 | AA | 52.4 ± 5.7 | 51.5 ± 5.8 | 53.4 ± 5.9 | 52.9 ± 5.1 | 52.8 ± 5.4 | 42.9 ± 5.0* |
| MDA-MB175VII ER− | AA | 51.3 ± 5.8 | 52.1 ± 5.2 | 51.3 ± 5.1 | 51.8 ± 5.1 | 51.6 ± 5.2 | 41.8 ± 4.9* |
| MDA-MB436 | CA | 24.2 ± 3.1 | 25.2 ± 3.2 | 24.6 ± 3.3 | 24.8 ± 3.1 | 23.9 ± 3.1 | 14.8 ± 1.1* |
| HCC1187 | CA | 25.1 ± 2.9 | 25.1 ± 2.1 | 25.2 ± 2.1 | 25.4 ± 2.2 | 24.8 ± 2.1 | 15.4 ± 1.2* |
| HCC1937 | CA | 22.2 ± 2.6 | 22.3 ± 2.7 | 22.9 ± 2.8 | 22.8 ± 2.1 | 22.6 ± 2.0 | 12.8 ± 1.9* |
| MDA-MB 157 | AA | 15.4 ± 2.1 | 15.2 ± 2.2 | 16.1 ± 2.3 | 15.0 ± 2.4 | 14.9 ± 2.5 | 5.0 ± 0.4* |
| HCC 70 | AA | 15.9 ± 1.9 | 16.1 ± 1.8 | 16.4 ± 1.4 | 16.3 ± 1.2 | 16.2 ± 1.3 | 6.3 ± 0.2* |
| HCC 2157 | AA | 15.1 ± 1.8 | 14.9 ± 1.9 | 16.1 ± 1.7 | 15.9 ± 1.6 | 15.2 ± 1.9 | 5.9 ± 0.3* |

TABLE 4.2

| sample type | | Temperature: 37° C. | | | | | |
|---|---|---|---|---|---|---|---|
| | | NOHA concentration (nM) in Days after incubation | | | | | |
| Control | ethnicity | 1 | 3 | 7 | 10 | 12 | 14 |
| mammary cells | CA | 62.9 ± 6.2 | 63.1 ± 6.3 | 63.7 ± 6.4 | 44.3 ± 5.2* | 36.8 ± 6.1* | 21.1 ± 7.1* |
| mammary cells ER+ | AA | 61.3 ± 7.0 | 62.4 ± 6.9 | 60.9 ± 6.2 | 39.9 ± 5.7* | 32.6 ± 5.8* | 29.4 ± 6.2* |
| BT483 | CA | 54.3 ± 5.7 | 54.7 ± 5.5 | 54.3 ± 5.1 | 32.9 ± 4.6* | 34.8 ± 6.7* | 23.6 ± 6.4* |
| MCF7 | CA | 54.9 ± 5.9 | 55.6 ± 5.9 | 55.7 ± 5.3 | 34.1 ± 5.0* | 34.1 ± 5.0* | 15.2 ± 5.2* |
| HCC1007 | AA | 53.1 ± 5.8 | 51.8 ± 5.6 | 53.1 ± 5.4 | 32.5 ± 4.7* | 30.4 ± 4.8* | 12.8 ± 5.2* |
| MDA-MB175VII ER− | AA | 52.4 ± 5.6 | 51.9 ± 5.5 | 51.7 ± 5.2 | 31.8 ± 3.8* | 32.6 ± 4.9* | 11.6 ± 5.2* |
| MDA-MB436 | CA | 23.7 ± 2.7 | 23.6 ± 2.2 | 24.4 ± 2.3 | 13.7 ± 1.3* | 8.4 ± 1.7* | BD* |
| HCC1187 | CA | 24.9 ± 2.5 | 25.3 ± 2.6 | 24.7 ± 2.8 | 14.5 ± 1.1* | 11.2 ± 1.9* | BD* |
| HCC1937 | CA | 22.9 ± 2.8 | 23.2 ± 2.5 | 23.1 ± 2.4 | 10.3 ± 0.9* | 10.4 ± 1.1* | BD* |
| MDA-MB 157 | AA | 15.2 ± 2.1 | 15.1 ± 1.7 | 16.0 ± 1.7 | 2.0 ± 0.4* | BD* | BD* |
| HCC 70 | AA | 16.1 ± 1.9 | 16.0 ± 1.7 | 15.9 ± 1.8 | 3.3 ± 0.2* | BD* | BD* |
| HCC 2157 | AA | 14.9 ± 1.8 | 15.4 ± 1.8 | 15.6 ± 1.6 | BD* | BD* | BD* |

TABLE 4.3

| sample type | | Temperature: 4° C. | | | | | |
|---|---|---|---|---|---|---|---|
| | | NOHA concentration (nM) in Days after incubation | | | | | |
| Control | ethnicity | 1 | 3 | 7 | 10 | 12 | 14 |
| mammary cells | CA | 63.2 ± 6.8 | 64.1 ± 7.1 | 61.4 ± 7.2 | 61.3 ± 7.2 | 61.7 ± 6.9 | 61.0 ± 6.8 |
| mammary cells ER+ | AA | 62.1 ± 7.1 | 62.4 ± 6.7 | 61.7 ± 7.2 | 63.1 ± 6.8 | 62.4 ± 7.2 | 61.8 ± 7.1 |
| BT483 | CA | 55.1 ± 7.2 | 54.9 ± 7.0 | 54.3 ± 6.8 | 54.9 ± 7.0 | 54.6 ± 7.1 | 55.4 ± 6.9 |
| MCF7 | CA | 54.8 ± 5.6 | 55.1 ± 6.3 | 54.9 ± 6.1 | 55.9 ± 5.7 | 54.8 ± 5.4 | 55.5 ± 5.8 |

TABLE 4.3-continued

Temperature: 4° C.

| sample type Control | ethnicity | NOHA concentration (nM) in Days after incubation | | | | | |
|---|---|---|---|---|---|---|---|
| | | 1 | 3 | 7 | 10 | 12 | 14 |
| HCC1007 | AA | 53.1 ± 5.7 | 52.7 ± 6.1 | 52.4 ± 5.8 | 53.5 ± 5.7 | 53.4 ± 5.3 | 53.3 ± 5.1 |
| MDA-MB175VII ER– | AA | 52.1 ± 5.1 | 50.7 ± 6.0 | 51.8 ± 5.4 | 52.1 ± 6.2 | 49.8 ± 7.1 | 50.8 ± 5.0 |
| MDA-MB436 | CA | 23.5 ± 2.7 | 23.9 ± 2.9 | 24.3 ± 3.1 | 23.8 ± 2.6 | 24.1 ± 2.8 | 24.0 ± 3.2 |
| HCC1187 | CA | 24.7 ± 2.9 | 25.6 ± 2.7 | 24.9 ± 2.9 | 25.1 ± 2.3 | 24.6 ± 2.7 | 25.1 ± 2.8 |
| HCC1937 | CA | 23.1 ± 2.4 | 22.9 ± 2.5 | 23.9 ± 2.7 | 23.4 ± 3.0 | | 24.0 ± 2.6 |
| MDA-MB 157 | AA | 14.9 ± 1.9 | 15.6 ± 1.7 | 15.9 ± 1.2 | 15.4 ± 1.5 | 15.0 ± 1.8 | 15.8 ± 1.6 |
| HCC 70 | AA | 15.1 ± 1.8 | 15.7 ± 1.6 | 15.8 ± 1.9 | 16.0 ± 1.8 | 15.2 ± 1.4 | 16.0 ± 2.1 |
| HCC 2157 | AA | 15.9 ± 1.7 | 15.2 ± 2.0 | 15.7 ± 1.7 | 15.4 ± 1.6 | 15.5 ± 1.8 | 15.4 ± 1.4 |

TABLE 4.4

Temperature: 42° C.

| sample type Control | ethnicity | NOHA concentration (nM) in Days after incubation | | | | | |
|---|---|---|---|---|---|---|---|
| | | 1 | 3 | 7 | 10 | 12 | 14 |
| mammary cells | CA | 62.7 ± 6.7 | 62.8 ± 7.2 | 40.1 ± 5.7* | 29.6 ± 4.2* | 11.7 ± 1.0* | BD* |
| mammary cells ER+ | AA | 61.9 ± 6.8 | 61.9 ± 7.0 | 37.9 ± 4.9* | 32.9 ± 5.3* | 19.2 ± 1.1* | BD* |
| BT483 | CA | 54.4 ± 5.8 | 54.2 ± 6.1 | 35.4 ± 5.6* | 32.1 ± 6.2* | 12.1 ± 1.3* | BD* |
| MCF7 | CA | 55.0 ± 6.1 | 54.8 ± 5.9 | 41.0 ± 7.2* | 33.4 ± 5.7* | 14.3 ± 1.2* | BD* |
| HCC1007 | AA | 52.8 ± 5.9 | 52.1 ± 5.4 | 36.8 ± 6.6* | 30.1 ± 6.2* | 12.8 ± 1.0* | BD* |
| MDA-MB175VII ER– | AA | 52.2 ± 5.4 | 51.6 ± 5.3 | 33.1 ± 5.8* | 26.9 ± 5.4* | 9.8 ± 1.0* | BD* |
| MDA-MB436 | CA | 24.0 ± 2.7 | 24.8 ± 2.2 | 7.2 ± 0.9* | 1.8 ± 0.1* | BD* | BD* |
| HCC1187 | CA | 24.6 ± 2.6 | 24.9 ± 2.8 | 8.7 ± 1.0* | 1.5 ± 0.1* | BD* | BD* |
| HCC1937 | CA | 22.9 ± 2.3 | 22.8 ± 2.5 | 5.4 ± 0.8* | 0.9 ± 0.1* | BD* | BD* |
| MDA-MB 157 | AA | 15.1 ± 1.8 | 15.3 ± 1.6 | 1.2 ± 0.5* | BD* | BD* | BD* |
| HCC 70 | AA | 15.7 ± 1.6 | 15.8 ± 1.8 | BD* | BD* | BD* | BD* |
| HCC 2157 | AA | 15.6 ± 1.4 | 15.1 ± 1.9 | BD* | BD* | BD* | BD* |

TABLE 4.5

Temperature: (negative 20° C.)

| sample type Control | ethnicity | NOHA concentration (nM) in Days after incubation | | | | | |
|---|---|---|---|---|---|---|---|
| | | 1 | 3 | 7 | 10 | 12 | 14 |
| mammary cells | CA | 62.5 ± 6.4 | 61.7 ± 7.1 | 63.1 ± 7.2 | 62.8 ± 6.6 | 62.6 ± 7.0 | 61.8 ± 7.2 |
| mammary cells ER+ | AA | 61.8 ± 6.9 | 62.6 ± 6.7 | 62.0 ± 6.9 | 61.9 ± 6.7 | 62.5 ± 6.4 | 62.7 ± 6.8 |
| BT483 | CA | 54.7 ± 7.1 | 54.3 ± 6.8 | 54.9 ± 7.2 | 53.8 ± 7.1 | 55.1 ± 6.8 | 54.5 ± 6.6 |
| MCF7 | CA | 55.4 ± 6.1 | 53.5 ± 6.3 | 54.7 ± 5.9 | 51.2 ± 5.6 | 53.9 ± 6.2 | 54.8 ± 6.3 |
| HCC1007 | AA | 52.9 ± 5.6 | 52.6 ± 6.1 | 53.5 ± 5.8 | 52.9 ± 6.0 | 53.1 ± 5.7 | 52.8 ± 5.8 |
| MDA-MB175VII ER– | AA | 51.9 ± 5.5 | 51.3 ± 5.7 | 50.9 ± 5.3 | 52.0 ± 6.0 | 51.2 ± 5.4 | 51.1 ± 5.1 |
| MDA-MB436 | CA | 23.9 ± 3.0 | 24.2 ± 2.8 | 24.5 ± 3.1 | 24.1 ± 2.9 | 24.0 ± 2.6 | 24.3 ± 2.5 |
| HCC1187 | CA | 25.0 ± 2.8 | 25.3 ± 2.6 | 25.1 ± 2.7 | 24.8 ± 2.5 | 24.9 ± 2.7 | 25.4 ± 2.8 |
| HCC1937 | CA | 22.8 ± 2.5 | 22.7 ± 2.3 | 23.4 ± 2.5 | 23.1 ± 2.7 | 23.2 ± 2.4 | 22.9 ± 2.3 |
| MDA-MB 157 | AA | 15.0 ± 1.7 | 15.4 ± 1.8 | 15.7 ± 2.1 | 14.9 ± 1.8 | 15.2 ± 1.6 | 15.4 ± 1.7 |
| HCC 70 | AA | 16.0 ± 1.8 | 15.9 ± 1.5 | 15.4 ± 1.6 | 15.8 ± 1.8 | 15.9 ± 1.8 | 15.7 ± 1.9 |
| HCC 2157 | AA | 15.4 ± 1.6 | 15.0 ± 1.7 | 15.9 ± 1.7 | 15.2 ± 1.6 | 15.3 ± 1.4 | 15.5 ± 1.6 |

TABLE 4.6

Temperature: (negative 80° C.)

| sample type Control | ethnicity | NOHA concentration (nM) in Days after incubation | | | | | |
|---|---|---|---|---|---|---|---|
| | | 1 | 3 | 7 | 10 | 12 | 14 |
| mammary cells | CA | 61.8 ± 6.8 | 63.1 ± 6.4 | 62.7 ± 6.3 | 61.6 ± 7.1 | 61.9 ± 7.2 | 61.5 ± 6.8 |
| mammary cells ER+ | AA | 60.9 ± 7.1 | 61.7 ± 6.9 | 61.5 ± 6.6 | 61.3 ± 6.4 | 60.8 ± 6.8 | 61.4 ± 6.5 |
| BT483 | CA | 53.8 ± 6.2 | 53.3 ± 6.5 | 53.7 ± 6.1 | 52.4 ± 6.8 | 53.5 ± 6.8 | 53.1 ± 6.9 |
| MCF7 | CA | 54.2 ± 5.6 | 54.6 ± 5.9 | 54.8 ± 5.7 | 55.0 ± 5.2 | 54.2 ± 5.7 | 54.8 ± 5.6 |
| HCC1007 | AA | 53.4 ± 5.1 | 53.6 ± 5.3 | 54.0 ± 5.2 | 53.9 ± 5.7 | 53.8 ± 5.4 | 53.6 ± 5.8 |
| MDA-MB175VII ER- | AA | 51.7 ± 5.3 | 51.9 ± 5.9 | 51.6 ± 5.1 | 51.9 ± 5.7 | 51.3 ± 5.1 | 51.7 ± 5.6 |
| MDA-MB436 | CA | 23.8 ± 2.7 | 25.0 ± 2.4 | 24.9 ± 2.6 | 24.1 ± 2.7 | 23.8 ± 2.6 | 24.7 ± 2.5 |
| HCC1187 | CA | 24.8 ± 2.6 | 25.2 ± 2.6 | 24.9 ± 2.9 | 25.2 ± 2.7 | 24.7 ± 2.4 | 25.2 ± 2.8 |
| HCC1937 | CA | 22.6 ± 2.8 | 22.9 ± 2.8 | 23.6 ± 2.8 | 23.2 ± 2.4 | 22.9 ± 2.6 | 23.1 ± 2.7 |
| MDA-MB 157 | AA | 14.8 ± 2.0 | 15.5 ± 2.6 | 16.2 ± 1.8 | 15.2 ± 1.8 | 14.9 ± 1.7 | 15.1 ± 1.2 |
| HCC 70 | AA | 16.1 ± 1.9 | 15.7 ± 1.7 | 16.1 ± 1.7 | 15.9 ± 1.6 | 16.1 ± 1.8 | 15.8 ± 1.5 |
| HCC 2157 | AA | 15.2 ± 1.6 | 14.9 ± 1.7 | 15.7 ± 1.8 | 15.4 ± 1.6 | 15.8 ± 1.9 | 15.6 ± 1.7 |

Example 4: Monoclonal NOHA Antibody Preparation and Protein Sequence

Antibody creation: Custom primary monoclonal antibody for NOHA was developed from Pierce Thermo Fisher (Grand island, NY). 5 mg of NOHA was conjugated with 2 mg keyhole limpet hemocyanin (KLH), for the preparation of NOHA antigen. KLH conjugated NOHA was then injected in to 5 mice to measure the intensity of the immune response. After 8 weeks from the time of inoculation, the mice bleeds were collected and analyzed for total IgG and IgM reaction at 1:100, 1:1000, 1:2000, and 1:10,000 dilution. Bleed samples with a titer score of ≥1 at 1:10,000 dilution (for both IgG and IgM) were used for hybridoma fusion that involved splenocytes from mice; and was subsequently sequenced. The molecular weight of the prepared custom monoclonal antibody for NOHA was identified to be 11848.96 Daltons.

Protein sequence: The monoclonal antibody for NOHA had a SEQ. ID. No. 1.

This sequence was analyzed using IgBlast database, and the results are presented in FIG. 4 and below. The IgBLAST search shows a very low bit-score and E-value, which are both suggestive of the high-level of uniqueness of the present sequence from those already documented in the database. The results further show a 88.2% similarity score to a human immunoglobulin kappa variable region, which is suggestive of identifying it as an immunoglobulin (viz., antibody).

| Length = 321 | | |
|---|---|---|
| Sequences producing significant alignments: | Score (Bits) | E Value |
| IGKV1D-43*01 germline gene Domain classification requested: imgt | 22.1 | 8.6 |

V-(D)-J rearrangement summary for query sequence (multiple equivalent top matches having the same score and percent identify, if present, as separated by a comma):

| Top V gene match | Top J gene match | Chain type | stop codon | V-J frame | Productive | Strand |
|---|---|---|---|---|---|---|
| IGKV1D-43*01 | N/A | VR | No | | | + |

V-(D)-J junction details based on top germline gene matches:

| V region end | V-J junction* | J region start |
|---|---|---|
| AGCCC | | |

*Overlapping nucleotides may exist at V-D-J junction (i.e. nucleotides that could be assigned to either rearranging gene). Such nucleotides are indicated inside a parenthesis (i.e. (TACAT)) but are not included under the V, D or J gene itself.

Alignment summary between query and top germline V gene hit:

| | from | to | length | matches | mismatches | gaps | identity (%) |
|---|---|---|---|---|---|---|---|
| FR2-IMGT | 271 | 287 | 17 | 15 | 2 | 0 | 88.2 |
| Total | | | 17 | 15 | 2 | 0 | 88.2 |

The antibody for NOHA had a very low bit-score and E-value, which is suggestive of the high-level of uniqueness of the present sequence from those already documented in the database.

Example 5: NOHA ELISA Method Validation

Figure 5:
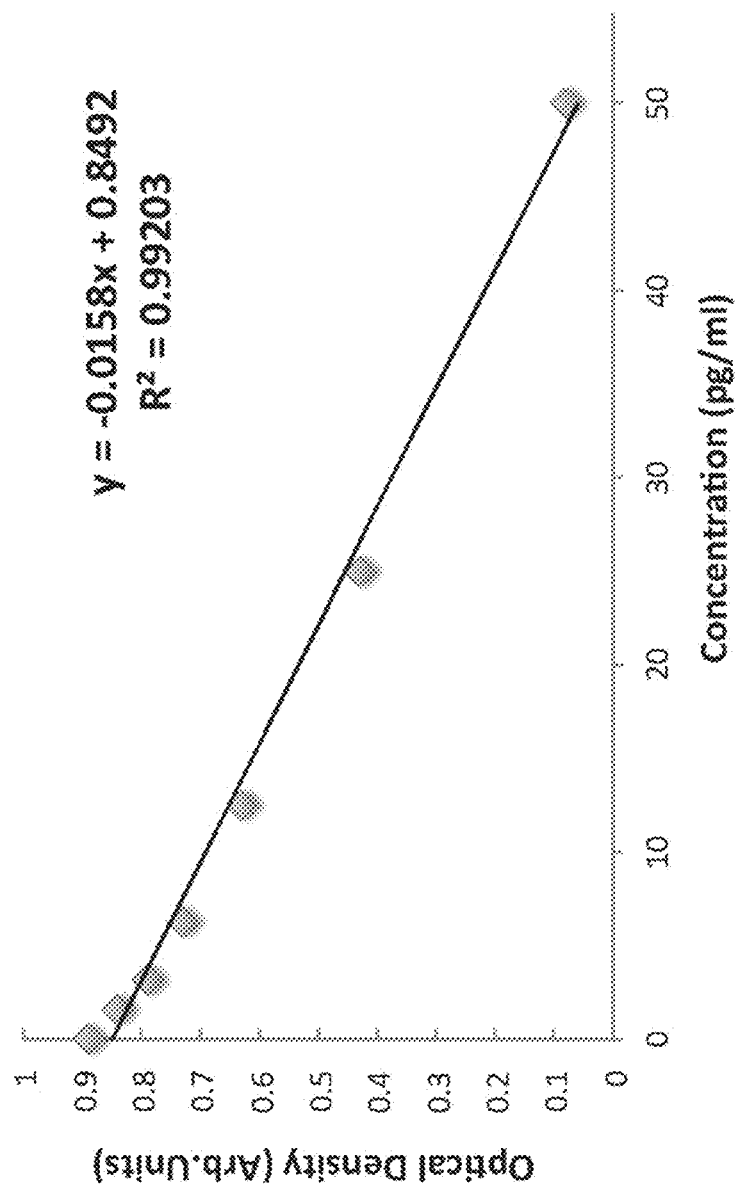
FIG. 5 illustrates a NOHA inverse ELISA standard curve.

ELISA Method. 50 µl of NOHA standard sample concentration prepared in Locke's buffer (viz., 10 mM HEPES, 5.6 mM KCl, 154 mM NaCl, 5.6 mM glucose, 1.2 mM MgCl2, 2.3 mM CaCl2, pH 7.4) was mixed with 50 µl of primary NOHA antibody serum (at 1:200 dilution, Pierce Thermo Fisher) and incubated for 30 min at 4° C. The mixture was added to a 96 well plate pre-coated with 100 NOHA (at 100 pg/ml concentration, in Locke's buffer). The plate was then incubated for 1 hour on a plate-rotator at 500 rpm, at 2-8° C. After incubation, the well content was aspirated, and the wells were washed three times with 200 µl ice-cold wash buffer (10 mM phosphate buffer pH 7.4, 150 mM NaCl, 0.05% Tween 20). 100 µl of enzyme conjugated secondary antibody (at 1:20,000 dilution in wash buffer) was added, and incubated for 1 hour on a plate rotator at 500 rpm, at 2-8° C. At the end of this incubation, the wells were washed again three times with 200 µl ice-cold wash buffer. 100 µl of substrate for peroxidase conjugated secondary antibody (viz., SIGMAFAST™ OPD) was added to each well, and incubated for 15 min in dark (by covering it with aluminum foil). At the end of this incubation, the reaction was stopped with 50 µl of 2N sulfuric acid. The plates were then read at 450 nm, within 10 min after adding stop solution. Based on the optical density the standard curve was generated, as shown in FIG. 5.

Quality control. NOHA Monoclonal antibody specificity. To determine the level of NOHA binding specificity, sample mixtures containing predetermined quantity of NOHA and varying concentration of structurally similar amino acids (viz., L-Arginine, L-lysine) was prepared. The structurally similar amino acid in these sample mixtures were of at least $8 \times 10^6$ higher concentration than the amount of NOHA that would be present. 100 µl of the sample mixture was co-incubated with 100 µl of 1:1000 diluted NOHA monoclonal antibody, for 1 hour; and then subjected to a competitive ELISA protocol. The results (as indicated in Table 5A) shows almost 100% antibody specificity to NOHA, even in the presence of very high concentrations of structurally similar amino acids.

TABLE 5A

NOHA inverse ELISA Antibody specificity analysis.

| NOHA concentration (pg/ml) | Spiked Varying L-Arginine/ L-Lysine (mM) | Observed NOHA detection in the presence of L-Arginine | Observed NOHA detection in the presence of L-lysine | recovery (%) in the presence of L-Arginine | recovery (%) in the presence of L-Lysine |
|---|---|---|---|---|---|
| 6.25 | 0.05 | 6.64 | 6.57 | 106.24 | 105.12 |
| 6.25 | 0.3 | 6.52 | 6.71 | 104.32 | 107.36 |
| 6.25 | 0.5 | 6.19 | 6.44 | 99.04 | 103.04 |
| 6.25 | 0.75 | 6.37 | 6.16 | 101.92 | 98.56 |
| 6.25 | 1 | not detected | not detected | not detected | not detected |

Linearity. Two NOHA samples of different concentrations (viz., sample 1, at 3.13 pg/ml; and sample 2, at 25 pg/ml) were diluted with each other at various proportions and assayed for recovery percentage (Table 5B). These results shows a recovery percent deviation of ≤6% between the observed and expected concentration range.

TABLE 5B

NOHA inverse ELISA linearity analysis (n = 4)

| Dilution ratio | | | | | |
|---|---|---|---|---|---|
| sample | sample 2 | Expected (pg/ml) | Optical density | Observed (pg/ml) | Recovery % |
| 100% | 0% | 3.13 | 0.79 | 3.22 | 103.012323 |
| 90% | 10% | 5.32 | 0.77 | 4.82 | 90.6356801 |
| 80% | 20% | 7.48 | 0.72 | 7.69 | 102.771026 |
| 70% | 30% | 9.67 | 0.70 | 9.28 | 96.0165997 |
| 60% | 40% | 11.86 | 0.65 | 12.18 | 102.706905 |
| 50% | 50% | 14.05 | 0.63 | 13.78 | 98.068124 |
| 40% | 60% | 16.24 | 0.58 | 16.67 | 102.677372 |
| 30% | 70% | 18.43 | 0.54 | 19.57 | 106.191204 |
| 20% | 80% | 20.62 | 0.52 | 20.52 | 99.511255 |
| 10% | 90% | 22.81 | 0.49 | 22.77 | 99.8075576 |
| 0% | 100% | 25 | 0.46 | 24.36 | 97.4545455 |

Precision. The inter-assay and intra-assay precision were determined from the mean of 6 replicates each (Tables 5C and Table 5D). These results shows a standard deviation of ≤1.2 between the observed and expected concentration range.

TABLE 5C

NOHA inverse ELISA inter-batch assay precision analysis.
Inter-batch assay precision

| NOHA Standard Sample | Number of replicates (n = 6) | expected concentration (pg/ml) | observed concentration Mean (pg/ml) | std dev | % covariation |
|---|---|---|---|---|---|
| 2 | 6 | 25 | 25.72 | 1.264 | 5.6 |
| 4 | 6 | 6.25 | 6.54 | 0.716 | 12.2 |
| 6 | 6 | 1.56 | 1.28 | 0.327 | 14.6 |

TABLE 5D

NOHA inverse ELISA Intra-batch assay precision analysis.
Intra-batch assay precision

| NOHA Standard Sample | Number of replicates (n = 6) | expected concentration (pg/ml) | observed concentration Mean (pg/ml) | std dev | % covariation |
|---|---|---|---|---|---|
| 2 | 6 | 25 | 25.44 | 1.085 | 3.9 |
| 4 | 6 | 6.25 | 6.41 | 0.629 | 3.3 |
| 6 | 6 | 1.56 | 1.72 | 0.431 | 4.2 |

Recovery. Two known quantities of NOHA was spiked into an existing known sample NOHA concentration and assayed. Alternatively, four known NOHA concentration samples were diluted and assayed to determine the percentage recovery (Table 5E and Table 5F). These results show a deviation of ≤8% from the theoretical value with spiked samples, which was ≤13% for diluted samples.

TABLE 5E

NOHA inverse ELISA spiked sample recovery analysis.
Spiked sample recovery

| Standard Sample # | Known Quantities | Spiked Standard s of varying concentration (pg/ml) | Expected (pg/ml) | observed (pg/ml) | Recovery (%) |
|---|---|---|---|---|---|
| 2 | 25 | 25 | 50 | 51.5316456 | 103.063291 |
| 2 | 25 | 12.5 | 37.5 | 39.0316456 | 104.084388 |
| 2 | 25 | 6.25 | 31.25 | 32.7816456 | 104.901266 |
| 2 | 25 | 3.13 | 28.13 | 29.6616456 | 105.444883 |
| 5 | 3.13 | 12.5 | 15.63 | 17.1616456 | 109.799396 |
| 5 | 3.13 | 6.25 | 9.38 | 9.91164557 | 105.667863 |
| 5 | 3.13 | 3.13 | 6.26 | 6.79164557 | 108.492741 |
| 5 | 3.13 | 1.56 | 4.69 | 5.02164557 | 107.071334 |

TABLE 5F

NOHA inverse ELISA dilution sample recovery analysis.
Dilution sample recovery

| Standard Sample | Original concentration (pg/ml) | dilution factor | Expected Concentration (pg/ml) | Observed concentration (pg/ml) | Recovery (%) |
|---|---|---|---|---|---|
| 2 | 25 | X2 | 12.5 | 11.025 | 88.2 |
| 3 | 12.5 | X2 | 6.25 | 6.875 | 110 |
| 4 | 6.25 | X2 | 3.13 | 3.55 | 113.41853 |
| 5 | 3.13 | X2 | 1.56 | 1.775 | 113.782051 |

These quality control results thus confirm a sensitive inverse ELISA method for NOHA monitoring. Since it is a inverse ELISA method, the intensity is inversely correlated with the concentration. The functional sensitivity of the assay was found to be 1.73 pg/ml; which is at least 5-fold lower than the current LC-MS methodology.

NOHA Stability Analysis by ELISA Method

Figure 6A:
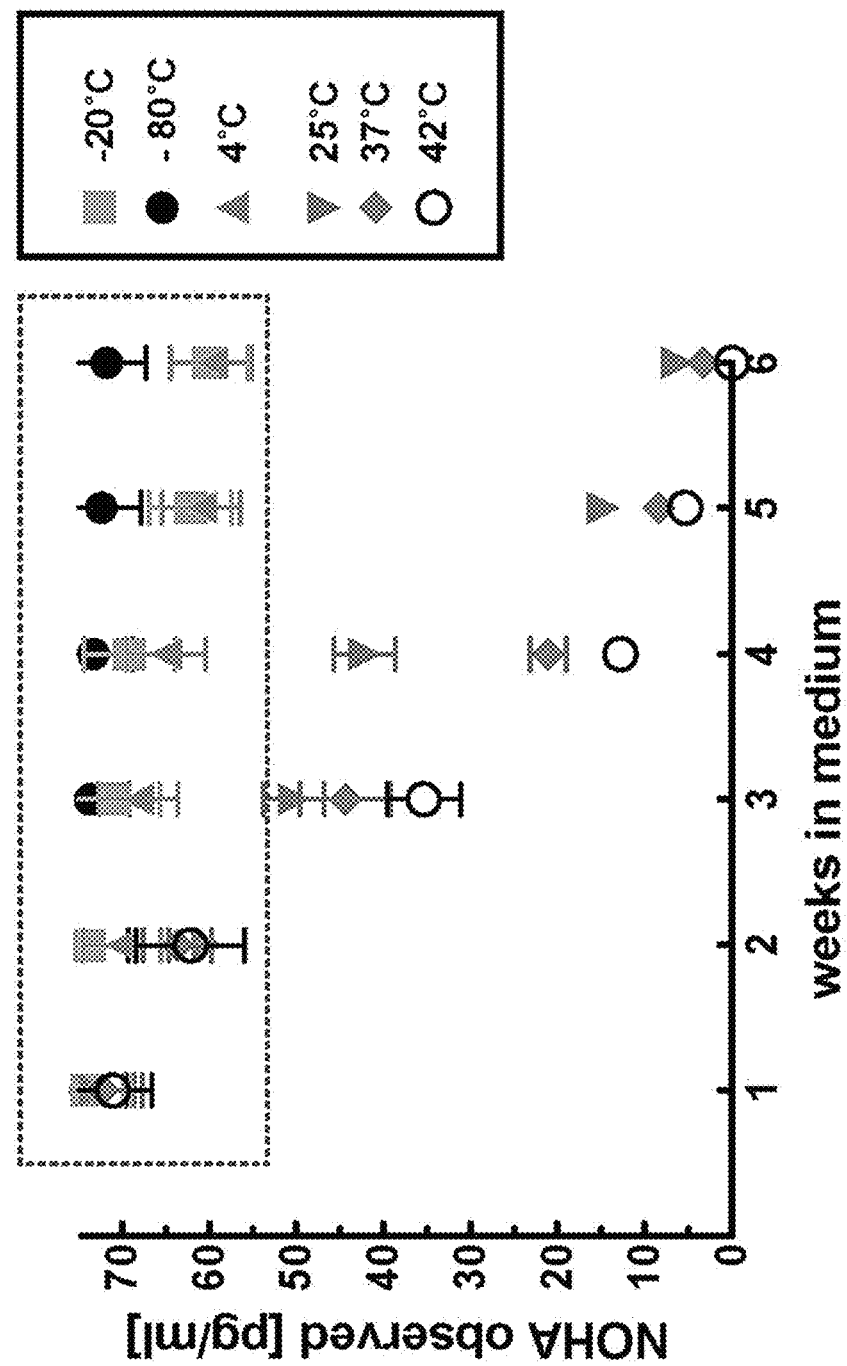
FIG. 6A presents an In Vitro medium NOHA stability analysis based on incubation duration and temperature condition for up to 6 weeks. n=4. Dotted rectangular box shows no significance in NOHA, P<0.01.

In vitro medium. To analyze NOHA stability via ELISA assay, medium was spiked with 75 pg/ml of NOHA and NOHA recovery was determined over 6 weeks at different temperatures (viz., −80° C., −20° C., 4° C., 25° C., 37° C. and 42° C.). NOHA was found to be stable over 6 week period when incubated at 4° C. and below (FIG. 6A). At higher temperatures (viz., 25° C., 37° C. and 42° C.), NOHA maintained stability for 1 week (FIG. 6A).

Plasma. When spiked with 75 pg/ml of NOHA, NOHA stability (measured as percentage recovery) was maintained with no significant changes in plasma for 7 days, at incubated temperatures of 37° C., 4° C. and −80° C. (FIG. 6B).

These results show the translatability of NOHA stability between culture medium and plasma samples, as analyzed by the ELISA assay.

NOHA Ethnic Diversity Predictability

Figure 7A:
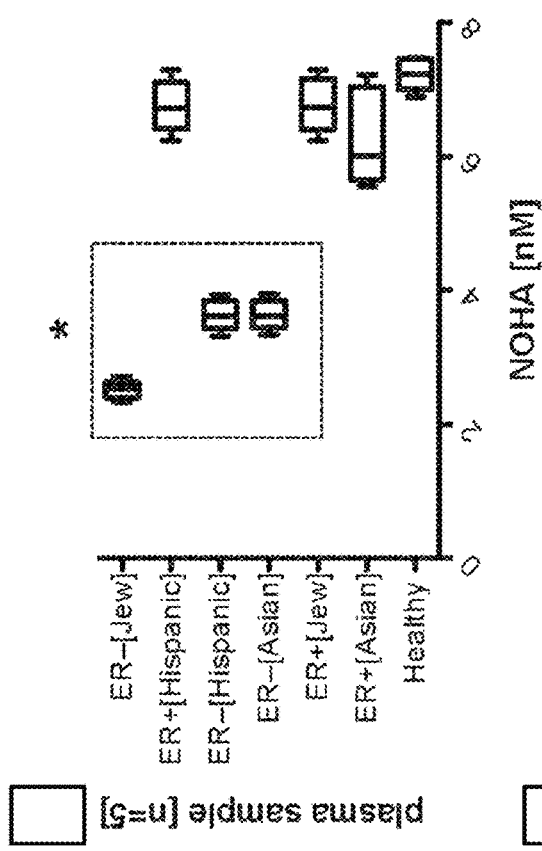
FIG. 7A and FIG. 7B present graphs of NOHA plasma level in ethnically disparate ER−/ER+ groups. *, Represents significance from ER+ and healthy groups, p<0.01.
Figure 7B:
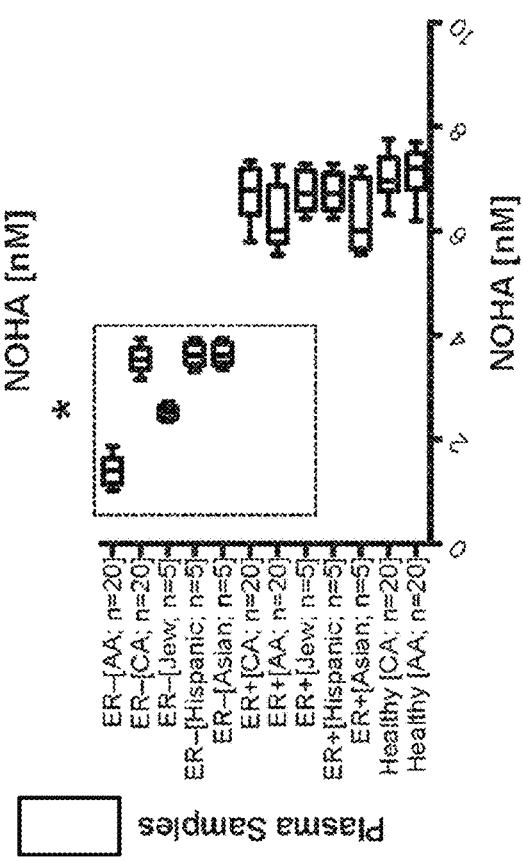

In addition to showing ethnic disparity in NOHA reduction between ER−[CA] versus ER− [AA]; when other ethnic races of Jewish, Asian and Hispanic origins were assessed for NOHA reduction based on Estrogen receptor expression, we identified a significant reduction in NOHA expression for ER− Jewish, Asian and Hispanic population compared to Healthy or ER+ groups (FIG. 7A). The level of NOHA reduction in ER− Jewish population was ≥24% more than those of ER− Asian or ER− Hispanic origin. However, the greatest NOHA reduction was seen with ER− AA groups (FIG. 7B). The level of NOHA reduction between ER− Asian, ER− Hispanic, and ER−[CA] origin were comparable to one another.

Medium NOHA Level Validation Over 9 Weeks by ELISA Method 3D spheroid medium samples collected for up to 9 weeks, showed a ≥0.85-fold reduction in ER−[CA] group after week 1, with a progressive reduction in NOHA of ≥3.9-fold from control or ER+ groups by week 9. Between week 1 and 9, the overall NOHA reduction in each of the ER−[CA] spheroid medium was ≥1.67-fold. ER−[AA] showed ≥1.9 fold reduction in NOHA after week 1, that reduced further by ≥9.4 fold from either control or ER+, by week 9. Between week 1 and 9, the overall NOHA reduction in each of the ER−[AA] spheroid medium was ≥2.62-fold (FIG. 8A).

Inhibitor Effect

The following inhibitory tests were performed to determine their role (and/or regulatory effect) on extra-tumoral NOHA accumulation. While NOHA is generated by NOS2 during nitric oxide production, it can be utilized in a NOS2 independent mechanism for nitric oxide generation, that could involve myeloperoxidase (MPO) mediated oxidation or cytochrome P450 reductase mediated pathway. Since NOHA is known to be a strong inhibitor of Arginase, and Arginase increase would favor tumor proliferation, the role of Arginase was also explored.

Nitric oxide synthase (NOS) inhibition. Spheroids incubated with an inhibitor for NOS, totally abolished NOHA measurement in the medium.

Arginases inhibition. Inhibition of Arginases with 5 nM 2(s)-amino-6-boronohexanoic acid (ABH) showed no significant disease specific or ethnic specific change in NOHA level from what was observed in the absence of 5 nM ABH inhibition (FIG. 8B).

Myeloperoxidase (MPO) inhibition. We used 20 µM of 4-Aminobenzoichydrazide, as the lowest effective inhibitory concentration; which showed a NOHA increase in the medium by ≥0.48 fold in ER−[CA]; and a ≥0.81-fold increase in medium NOHA level in ER−[AA] over a 9 week period (FIG. 8C).

Cytochrome P450 reductase inhibitor. We used 10 µM of micronazole salt, as the lowest effective inhibitory concentration; which showed a NOHA increase in the medium by ≥0.42 fold in ER−[CA]; and a ≥0.79-fold increase in medium NOHA level in ER−[AA] over a 9 week period (FIG. 8D).

3D Spheroid Assays

NOHA. No significant change in NOHA 3D spheroid level was evident after 1 week in any of the ethnic and disease specific groups.

Figure 9:
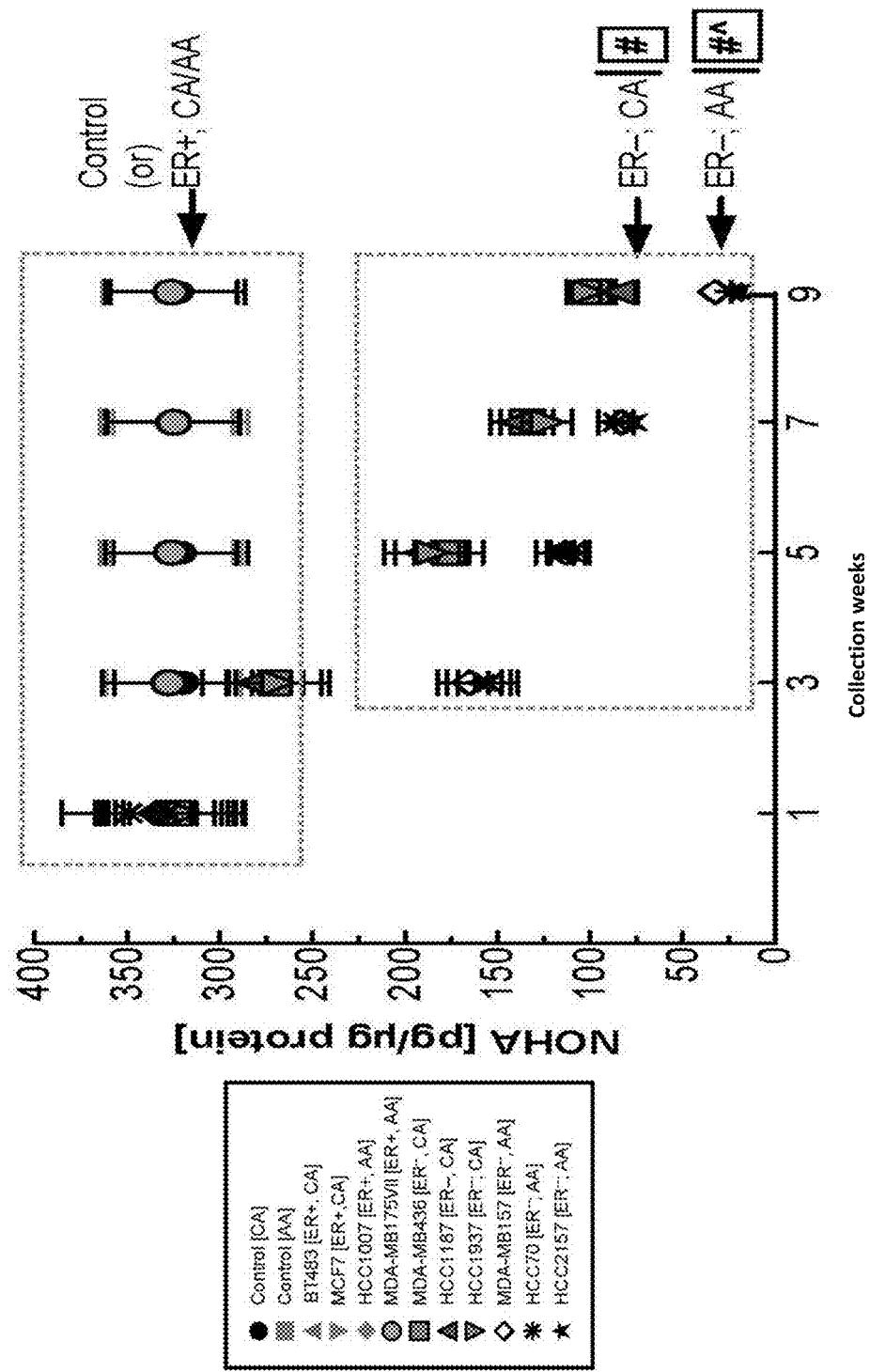
FIG. 9 presents a graph of NOHA level in 3D spheroids. #, represents significance from ER+ and control groups; and ^, represents significance from ER−[CA] groups. n=4. P<0.01

ER−[CA] showed ≥0.18-fold reduction in NOHA by week 3, with further reduction of ≥2.4-fold from control/ER+ by week 9. During the 9-week period, NOHA reduction within each of the 3 ER−[CA] was ≥1.8-fold (FIG. 9). ER−[AA] showed ≥0.9-fold reduction in NOHA by week 3, with further reduction of ≥9.0-fold from control/ER+ by week 9. During the 9-week period, NOHA reduction within each of the 3 ER−[AA] was ≥4.15-fold (FIG. 9).

NOS2 inhibition totally abolished NOHA measurement. Arginase Inhibition did not alter NOHA from as seen without inhibitory response. MPO/Cyto P450 inhibition, improved 3D Spheroid NOHA towards control conditions at ≥3 weeks.

NOS2 Expression.

ER−[CA] NOS2 expression increased by ≥1 fold by week 1; and by week 9, it further increased by ≥2.3 fold. Over 9 week period, the net increase in NOS2 for ER− CA is ≥0.57 fold. ER− [AA] NOS2 expression increased by ≥1.6 fold by week 1; and by week 9, it further increased by ≥3.2 fold. Over 9 week period, the net increase in NOS2 for ER− AA is ≥0.54 fold (FIG. 10A).

Inhibitor Study

Arginase inhibition. ER−[CA] NOS2 expression increased by ≥1.8-fold by week 1 and by week 9, it further increased by ≥3.4-fold. Over 9 week period, the net increase in NOS2 for ER− CA is ≥0.53 fold (FIG. 10B). When compared to ER− CA without Arginase inhibition, Arginase inhibition improved NOS2 expression by ≥0.3 over a 9 week period. ER−[AA] NOS2 expression increased by ≥2.6 fold by week 1 and by week 9, it further increased by ≥4.3 fold. Over 9 week period, the net increase in NOS2 for ER− AA is ≥0.6 fold. when compared to ER− AA without Arginase inhibition, Arginase inhibition improved NOS2 expression by ≥0.4 over a 9 week period (FIG. 10B).

ii. MPO inhibition. ER−[CA] NOS2 expression increased by ≥2.1 fold by week 1 and by week 9, it further increased by ≥3.9 fold. Over 9-week period, the net increase in NOS2 for ER− CA is ≥0.57-fold. When compared to ER−[CA] without MPO inhibition, MPO inhibition improved NOS2 expression by ≥0.5 fold over a 9-week period (FIG. 10C). ER−[AA] NOS2 expression increased by ≥3.3 fold by week 1 and by week 9, it further increased by 6.2-fold. Over 9-week period, the net increase in NOS2 for ER− AA is ≥0.65-fold. When compared to ER−AA without MPO inhibition, MPO inhibition improved NOS2 expression by ≥0.65 fold over a 9-week period (FIG. 10C).

iii. Cytochrome P450 reductase. ER−[CA] NOS2 expression increased by ≥2.2-fold by week 1 and by week 9, it further increased by ≥4.1 fold. Over 9-week period, the net increase in NOS2 for ER− CA is ≥0.59-fold. When compared to ER−CA without Cyto P450 inhibition, Cyto P450 inhibition improved NOS2 expression by ≥0.52-fold over a 9 week period (FIG. 10D). ER-[AA] NOS2 expression increased by ≥3.5-fold by week 1 and by week 9, it further increased by 6.4-fold. Over 9-week period, the net increase in NOS2 for ER- AA is ≥0.67-fold. When compared to ER-AA without Cyto P450 inhibition, Cyto P450 inhibition improved NOS2 expression by ≥0.69-fold over a 9 week period (FIG. 10D).

While there is distinction in the net increase in ER-[AA] versus ER-[CA], the overall increase between the weeks within a given ER- ethnic group of [AA] versus [CA], are similar; whether it would be with or without inhibitory effect.

NOS Activity.

Figure 11:
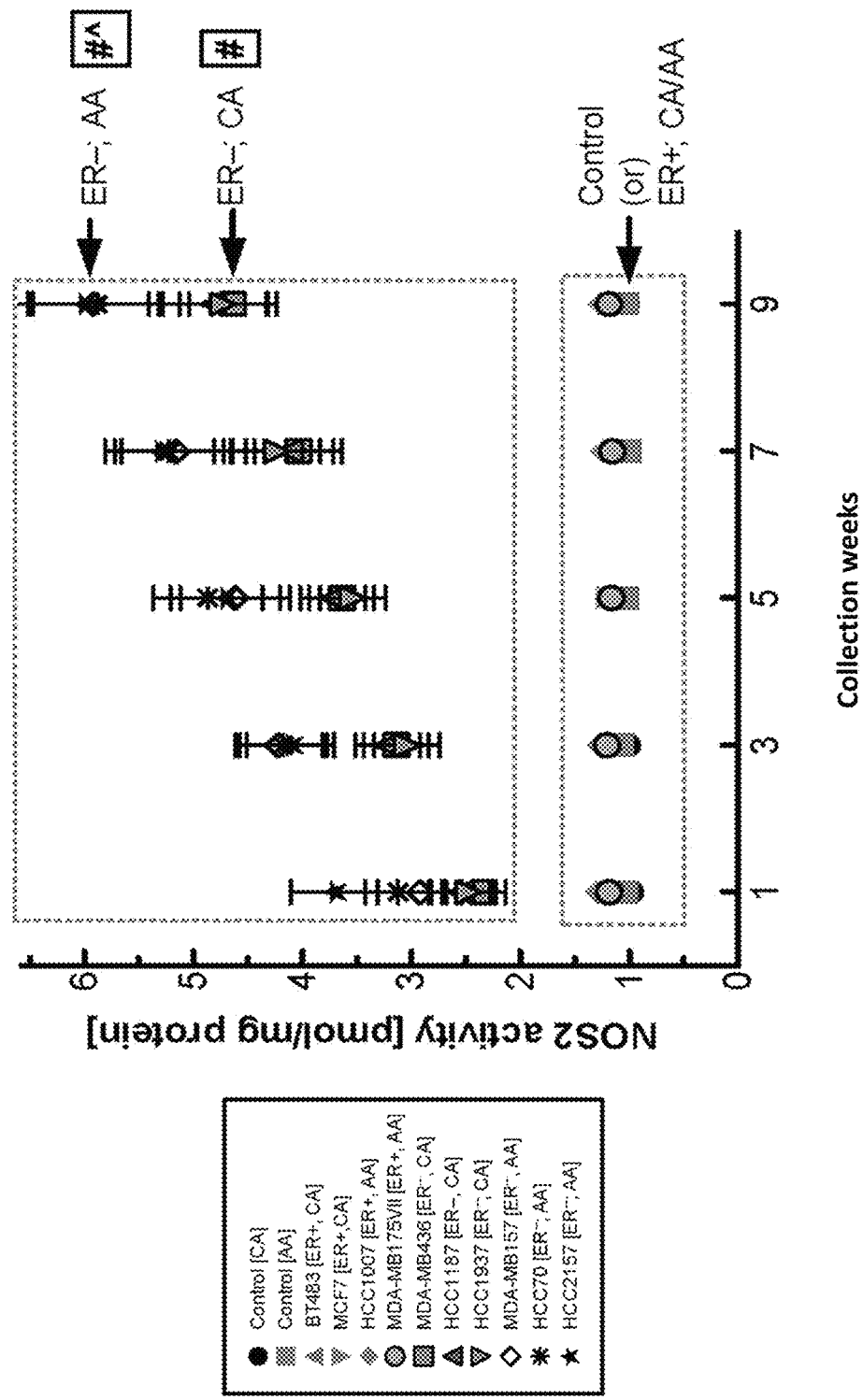
FIG. 11 presents an analysis of 3D spheroid NOS2 activity as total nitrite, #, represents significance from ER+ and control groups; and ^, represents significance from ER−[CA] groups. n=4. P<0.01.

ER-[CA] NOS2 activity increased by ≥1.0 fold by week 1 and continued to increase to ≥2.8 fold by week 9 (when compared to control). Over 9 week period, the net increase in NOS2 activity within ER- CA is ≥0.9 fold. ER-[AA] NOS2 activity increased by ≥1.5 fold by week 1 and continued to increase to ≥3.77 fold by week 9 (when compared to control). Over 9 week period, the net increase in NOS 2 activity within ER- AA is ≥0.89 fold (FIG. 11).

While there is distinction in the net increase in ER- AA versus ER- CA, when we look at the overall increase between the weeks within a given ER- ethnic group of AA versus CA, they are comparable (i.e., 0.9 versus 0.89 fold increase)

Inhibition Studies

Figures 12A, 12B:
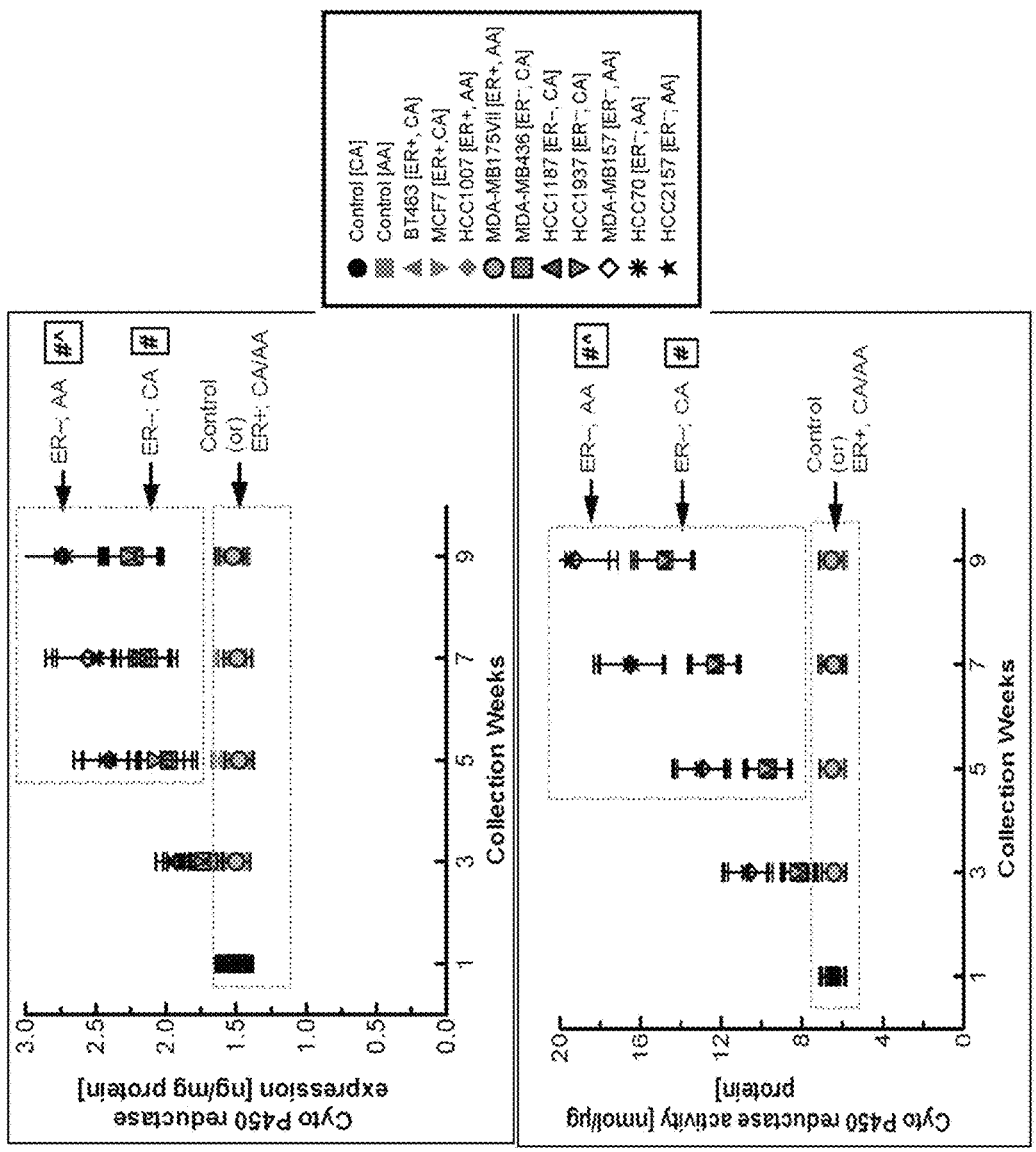
FIG. 12A and FIG. 12B present analysis of cytochrome P450 reductase.

Arginase Inhibition: improved NOS2 activity by ≥3 fold in ER- CA, and by 4 fold increase in ER- AA. MPO inhibition: improved NOS2 activity by 3.5 fold in ER-CA, and by ≥5.2 fold increase in ER-AA. Cyto P450 reductase inhibition: improved NOS2 activity by ≥3.4 fold in ER-CA, and by ≥5.7 fold increase in ER-AA. Cytochrome P450 reductase expression and activity i. Cytochrome P450 reductase expression. ER-[CA] shows ≥0.4 fold increase in cyto P450 reductase expression than in ER+ or control. ER-[AA] shows ≥0.7 fold increase in cyto P450 reductase expression than in ER+ or control. Compared to ER-[CA]; ER-[AA] shows ≥0.2 fold increase in cyto P450 reductase expression (FIG. 12A).

ii. Cytochrome P450 reductase activity. ER-[CA] shows ≥0.2 fold increase in Cyto P450 reductase activity by week 3, that rose to ≥1.2 fold increase by week 9 (than in control or ER+). ER- [AA] shows ≥0.6 fold increase in Cyto P450 reductase activity by week 3, that rose to ≥2.0 fold increase by week 9 (than in control or ER+). Compared to ER-[CA]; ER-[AA] shows ≥0.3 fold increase in cyto P450 reductase activity between weeks 3 and 9 (FIG. 12B).

MPO Expression and Activity i. MPO expression. ER-[CA] shows ≥0.3 fold increase in MPO expression than in ER+ or control. ER-[AA] shows ≥0.48 fold increase in MPO expression than in ER+ or control (FIG. 12A). Compared to ER-[CA]; ER-[AA] shows ≥0.2 fold increase in MPO expression.

ii. MPO activity. ER-[CA] shows ≥0.4 fold increase in MPO activity by week 3, that rose to ≥1.8 fold increase by week 9 (than in control or ER+). ER-[AA] shows ≥0.9 fold increase in MPO activity by week 3, that rose to ≥3.1 fold increase by week 9 (than in control or ER+). Compared to ER-[CA]; ER-[AA] shows ≥0.31 fold increase in MPO activity by week 3; which increased to ≥0.45 fold by week 9 (FIG. 13B).

Arginase Expression and Activity

Figure 14:
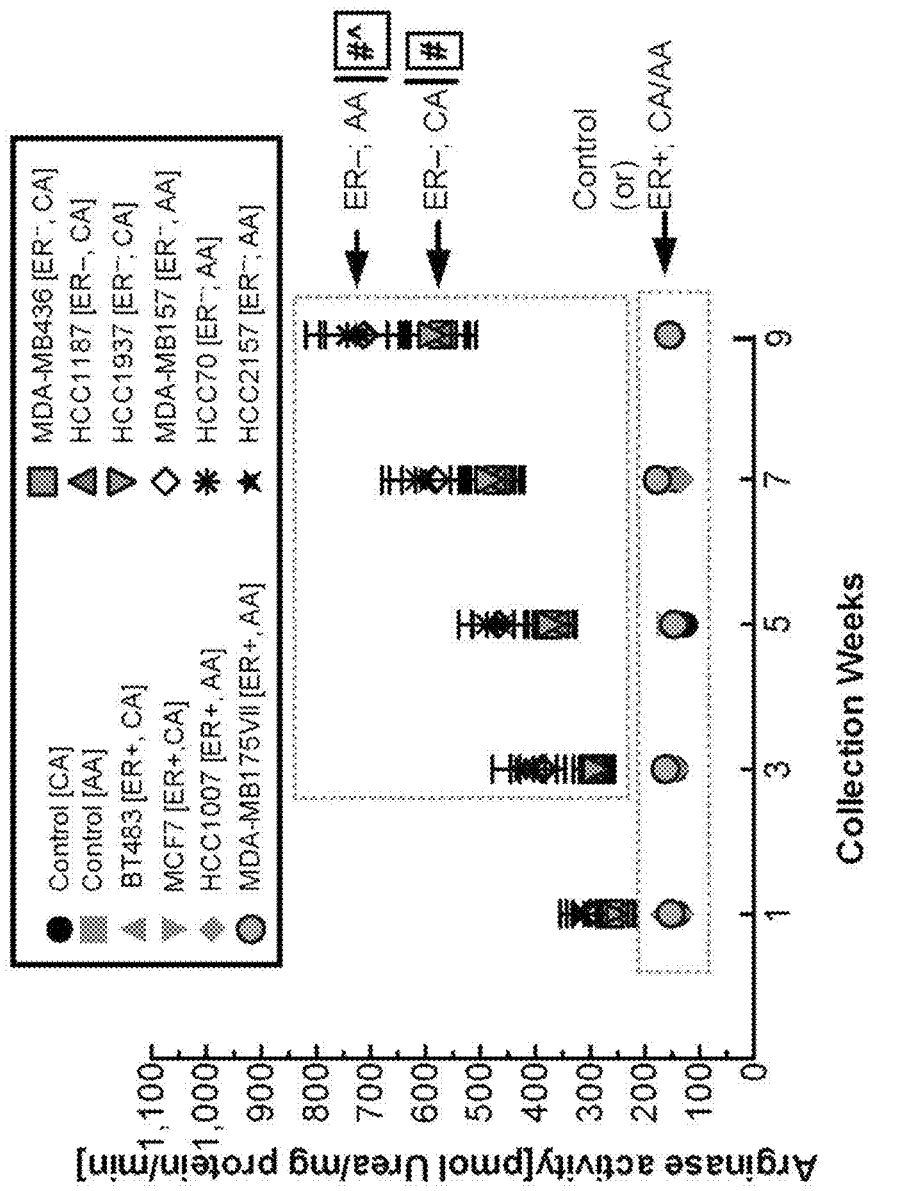
FIG. 14 presents analysis of Arginase activity. #, represents significance from ER+ and control groups; and ^, represents significance from ER−[CA] groups. n=4. P<0.01.

Activity. ER-[CA] showed ≥2 fold increase in Arginase activity, and ≥0.3 fold increase in Arginase expression after week 3, Between week 3 and 9, Arginase activity increased by ≥1.14 fold, and Arginase expression increased by ≥0.87 fold. ER-[AA] showed ≥2.5 fold increase in Arginase activity, and ≥0.4 fold increase in Arginase expression after week 3, Between week 3 and 9, Arginase activity increased by ≥1.36 fold, and Arginase expression increased by ≥0.92 fold (FIG. 14).

MPO or Cyto P450 inhibition caused a reduction in Arginase activity by ≥1 fold at week 3. Between week 3 and 9, Arginase activity increased by ≥2.4 fold. But no significant change in Arginase expression from control was observed during MPO or Cyto inhibition.

Arginase activity inhibition showed a net increase in both MPO and Cytochrome p450 expression and activity. MPO showed a ≥1.2 fold increase in its expression and activity, while Cytochrome P450 reductase showed an increase of ≥0.98 in its expression and activity after Arginase activity inhibition with 5 nM ABH.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A method of detecting a level of NOHA in a subject, the method comprising:
obtaining a subject sample from a subject; and
detecting a level of NOHA in the subject sample by contacting the subject sample with a NOHA antibody, or an antigen-binding fragment thereof, and detecting binding between NOHA and the NOHA antibody or the antigen-binding fragment thereof, wherein the NOHA antibody comprises the amino acid sequence of SEQ ID NO: 1.

2. The method of claim 1 further comprising comparing the level of NOHA in the subject sample to a level of NOHA in a control sample.

3. The method of claim 2 wherein the control sample is based on ethnic origin of the subject.

4. The method of claim 2 wherein the control sample is based on an expected state of the ER− breast cancer in the subject.

5. A method of monitoring ER− breast cancer in a subject, the method comprising:
obtaining a first subject sample from a subject suffering from breast cancer;
detecting a level of NOHA in the first subject sample by contacting the first subject sample with a NOHA antibody, or an antigen-binding fragment thereof, and detecting binding between NOHA and the NOHA antibody or the antigen-binding fragment thereof; and
comparing the level of NOHA obtained from the first subject sample to a level of NOHA in a control sample, wherein the NOHA antibody comprises the amino acid sequence of SEQ ID NO:1.

6. The method of claim 5 further comprising diagnosing the subject with ER− breast cancer if the level of NOHA in the first subject sample is lower than the level of NOHA in the control sample.

7. The method of claim 5 further comprising:
administering to the subject a treatment regimen;
obtaining a second subject sample subsequent to commencement of the treatment regimen;
detecting a level of NOHA in the second subject sample by contacting the second subject sample with a NOHA antibody, or an antigen-binding fragment thereof, and detecting binding between NOHA and the NOHA antibody or the antigen-binding fragment thereof; and
comparing the level of NOHA in the first subject sample and the second subject sample, wherein a higher level of NOHA in the second subject sample indicates the subject's responsiveness to the treatment regimen.

8. The method of claim 5 wherein the control sample is based on ethnic origin of the subject.

9. The method of claim 5 wherein the control sample is based on an expected state of the ER− breast cancer in the subject.

10. The method of claim 5 wherein the detecting is achieved with an immunoassay selected from a group consisting of affinity capture assay, immunometric assay, heterogeneous chemiluminscence immunometric assay, homogeneous chemiluminscence immunometric assay, ELISA, western blotting, radioimmunoassay, magnetic immunoassay, real-time immunoquantitative PCR (iqPCR), SERS label free assay and combinations thereof.

11. A method of monitoring ER− breast cancer in a subject, the method comprising:
obtaining a first subject sample from a subject suffering from breast cancer;
detecting a level of NOHA in the first subject sample by contacting the first subject sample with a NOHA antibody, or an antigen-binding fragment thereof, and detecting binding between NOHA and the NOHA antibody or the antigen-binding fragment thereof;
administering to the subject a treatment regimen;
obtaining a second subject sample subsequent to commencement of the treatment regimen;
detecting a level of NOHA in the second subject sample by contacting the second subject sample with a NOHA antibody, or an antigen-binding fragment thereof, and detecting binding between NOHA and the NOHA antibody or the antigen-binding fragment thereof; and
comparing the level of NOHA in the first subject sample and the second subject sample, wherein a higher level of NOHA in the second subject sample indicates the subject's responsiveness to the treatment regimen, wherein the NOHA antibody comprises the amino acid sequence of SEQ ID NO:1.

12. The method of claim 11 wherein the detecting is achieved with an immunoassay selected from a group consisting of affinity capture assay, immunometric assay, heterogeneous chemiluminscence immunometric assay, homogeneous chemiluminscence immunometric assay, ELISA, western blotting, radioimmunoassay, magnetic immunoassay, real-time immunoquantitative PCR (iqPCR), SERS label free assay and combinations thereof.

* * * * *